United States Patent [19]
Goodman et al.

[11] Patent Number: 6,096,710
[45] Date of Patent: Aug. 1, 2000

[54] COLLAGEN-LIKE PEPTOID RESIDUE-CONTAINING STRUCTURES

[75] Inventors: Murray Goodman, La Jolla; Joseph P. Taulane, San Diego; Yangbo Feng; Giuseppe Melacini, both of La Jolla, all of Calif.

[73] Assignee: The Regents of the University of California, Oakland, Calif.

[21] Appl. No.: 08/668,380

[22] Filed: Jun. 21, 1996

Related U.S. Application Data

[60] Provisional application No. 60/006,894, Nov. 17, 1995.

[51] Int. Cl.$^7$ .................................................. A61K 38/00
[52] U.S. Cl. ............................... 514/17; 514/18; 530/330
[58] Field of Search ................................ 514/3, 5, 10, 11, 514/15, 18, 17; 530/324, 326, 327, 328, 329, 331

[56] References Cited

U.S. PATENT DOCUMENTS

| | | | |
|---|---|---|---|
| 5,190,920 | 3/1993 | Eyal et al. | 514/17 |
| 5,200,397 | 4/1993 | Deutch et al. | 514/15 |
| 5,268,358 | 12/1993 | Fretto | 514/12 |
| 5,279,956 | 1/1994 | Griffin et al. | 514/12 |
| 5,358,934 | 10/1994 | Borovsky et al. | 530/330 |

FOREIGN PATENT DOCUMENTS

| | | | |
|---|---|---|---|
| 9310231 | 5/1993 | WIPO | 514/12 |

OTHER PUBLICATIONS

Germann, H.P., et al., A Synthetic Model of Collagen: An Experimental Investigation of the Triple–Helix Stability, (1988), Biopolymers, vol. 27, 157–163.

Morton, Laurence F., et al., Platelet Aggregation by a Collagen–Like Synthetic Peptide, (1993), Thrombosis Research 72; 367–372.

Ananthanarayanan, V.S., et al. (1976) Polypeptide models of collagen. Solution properties of (Gly–Pro–Sar)$_n$ and (Gly–Sar–Pro)$_n$. Biopolymers 15:707–716.

Anderson, S., et al. (1993) Expanding role for templates in synthesis. Acc. Chem Res. 26:469–475.

Bansal, M., et al. (1978) A theoretical study of the structures of (Gly–Pro–Leu)$_n$ and (Gly–Leu–Pro)$_n$. Peptide Protein Res. 11:73–81.

Bansal, M., et al. (1977) Stereochemical restrictions on the occurrence of amino acid residues in the collagen structure. Int. J. Peptide Protein Res. 9:224–234.

Bella, J., et al. (1994) Crystal and molecular structure of a collagen–like peptide at 1.9 Å resolution. Science 266:75–81.

Bhatnagar, R., et al. (1976) in Biochemistry of Collagen, Ramachandran, G.N. & Reddi, A.H. Eds., Plenum Press New York and London, pp. 479–514.

Buckus, P. (1964) The reaction of α–amino acids with acrylamide. Chem. Abstr. 61:5511b.

Bonora, G., et al. (1974) Sequential oligopeptides. Synthesis and characterization of the oligopeptides and a polypeptide with the repeating ... Biopolymers 13:1055–1066.

Brown, F.R., et al. (1969) Low temperature circular dichroism of poly (glycyl–L–prolyl–alanine). J. Mol. Biol. 39:307–313.

Fields, C., et al. (1992) Three–dimensional orthogonal solid– phase synthesis of cell–adhesive, triple–helical collagen– model peptides. Peptide Chem. Proc. of 2nd Japan Symp. on Peptide Chemistry 14–18.

Fields, C., et al. (1993) Solid–phase synthesis and stability of triple–helical peptides incorporating native collagen sequences. Biopolymers 33:1695–1707.

Goodman, M., et al. (1994) Synthesis and characterization of sequential peptide–peptoid copolymers. Polymer Preprints 35(1):767–768.

Ikeura, Y., et al. (1990) Molecular recognition at the interface. Synthesis and monolayer property of long–chain derivatives of kemp's acid. Chemistry Letters 169–172.

Inouye, K., et al. (1976) Effects of the stereo–configuration of the hydroxyl group in 4–hydroxyproline on the triple–helical structures formed by homogeneous peptides resembling collagen. Biochimica et Biophysica Acta 420:133–141.

Kelly, T.R., et al. (1990) Bisubstrate reaction templates. Examination of the consequences of identical versus different binding sites. Amer. Chem. Soc. 112:8024–8034.

Kemp, D., et al. (1981) Synthesis and conformational analysis of cis,cis–1,3,5–Trimethylcyclohexane–1,3,5–tricarboxylic acid. J. Org. Chem. 46:5140–5143.

Miller, M., et al. (1980) Calculation of the structures of collagen models. Role of interchain interactions in determining the triple–helical coiled–coil conformation . . . Macromolecules 13:910–913.

Müller, K., et al. (1993) Chap. 33 in Perspectives in Medicinal Chemistry. Verlag Helvetica Chimica Acta, Basel.

Mutter, M., et al. (1989) A chemical approach to protein design–template–assembled synthetic proteins (TASP). Angew. Chem. Int. Ed. Engl. 28:535–554.

Némethy, G., et al. (1980) Calculation of the structures of collagen models. Role of interchain interactions in determining the triple–helical coiled–coil conformation . . . Macromolecules 13:914–919.

Pei, Y., et al. (1994) Post–modification of peptoid side chains: [3+2] cycloaddition of nitrile oxides with alkenes and alkynes on the solid–phase. Tetrahedron Letters 35(32):5825–5828.

(List continued on next page.)

*Primary Examiner*—Cecilia J. Tsang
*Assistant Examiner*—Patrick R. Delaney
*Attorney, Agent, or Firm*—Pillsbury Madison & Sutro LLP; Anita M. Kirkpatrick

[57] ABSTRACT

Synthetic collagen in triple helical conformation and comprising amino acid chains of repeating trimers of highly populated collagen sequences as well as those sequences wherein the proline or hydroxyproline residue is replaced with a peptoid residue. The invention includes methods of preparing synthetic collagen structures having the triple helix conformation present in collagen from collagen-type polypeptides and poly(peptide-peptoid residue) chains by means of a helix-inducing template.

10 Claims, 4 Drawing Sheets

OTHER PUBLICATIONS

Rich, A., et al. (1955) The structure of collagen. Nature 176:915–916.

Rogers, T., et al. (1986) Glyphosate and glyphosate derivatives. Chem. Abstr. 105:226986z.

Roth, W., et al. (1980) Triple helix–coil transition of covalently bridged collagenlike peptides. Biopolymers 19:1909–1917.

Sakaibara, S., et al. (1968) Synthesis of poly–(L–prolyl–L––prolyglcycl) of defines molecular weights. Bull Chem. soc. Jap. 41(5):1273.

Sakakibara, S., et al. (1973) Synthesis of (Pro–Hyp–Gly)$_n$ of defined molecular weights. Biochimica et Biopysica Acta. 303:198–202.

Scatturin, A., et al. (1975) Conformational studies on sequential polypeptides. Part VI. Structural investigationon (Pro–Leu–Gly)$_{10}$, (Pro–Leu–Gly)$_n$ and (Leu–Pro–Gly)$_n$. Int. J. Peptide Protein Res. 7:425–435.

Segal, D.M., et al. (1969) Polymers of tripeptides as collagen models. J. Mol. Biol. 43:487–496.

Simon, R., et al. (1992) Peptoids: A modular approach to drug discovery. Proc. Natl. Acad. Sci. 89:9367–9371.

Tanaka, T., et al. (1993) A synthetic model of collagen structure taken from bovine macrophage scavenger receptor. FEBS 13257 334(3):272–276.

Tuchscherer, G., et al. (1993) The TASP concept: mimetics of peptide ligands, protein surfaces and folding units. Tetraderon Letters 49(17):3559–3575.

Tuchscherer, G. (1995) Journ. Peptide Sci. 1:3–10.

Venugopal, M., et al. (1994) Electrostatic interactions in collagen–like triple helical peptides. Biochemistry 33:7948–7956.

Vuillmeumier, S., et al. (1993) Synthetic peptide and template–assembled synthetic protein models of the hen egg white lysozyme 87–97 helix: importance of a protein–like framework . . . Biopolymers 33:389–400.

Walton, A.G., et al. (1973) Biopolymer Models. Biopolymers 428–433.

Zagari, A., et al. (1994) The effect of the –azetidine–2–carboxylic acid residue on protein conformation. IV Local substitutions in the collagen trriple helix. Biopolymers 34:51–60.

Zagari, A., et al. (1990) The effect of the L–Azetidine–2–carboxylic acid residue on protein conformation. III. Collagen–like poly(tripeptide)s. Biopolymers 30:967–974.

Zuckermann, R., et al. (1992) Efficient method for the preparation of peptoids [oligo(N–substituted glycines)] by submonomer solid–phase synthesis. J. Am. Chem. Soc. 114:10646–10647.

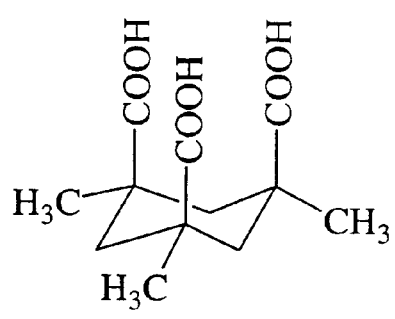
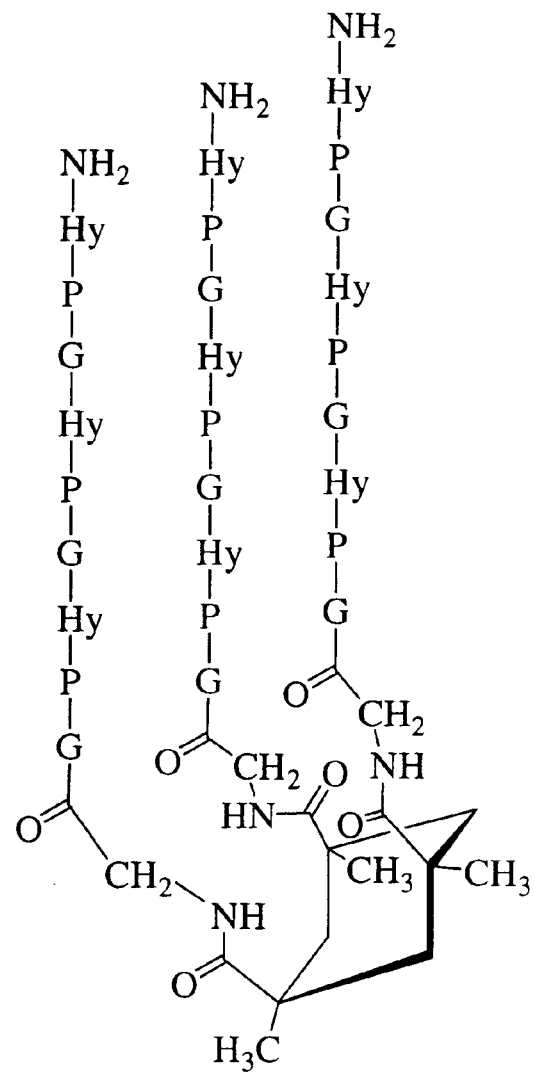
FIGURE 1a
FIGURE 1b

COLLAGEN-LIKE PEPTOID RESIDUE-CONTAINING STRUCTURES

This application claims benefit of priority to U.S. Provisional Application No. 60/006,894 filed on Nov. 17, 1995.

This work was supported in part by a National Science Foundation Grant No. DMR-9201133. The U.S. Government may have rights in the invention.

The present invention relates to synthetic collagen-like polymers comprising repeating trimeric amino acid sequences or trimeric sequences wherein one of the amino acids has been replaced by a peptoid residue. It relates specifically to synthetic collagen polymers having a collagen-like triple helical conformation which consists of three polyproline II-like chains. It also relates to the use of template molecules to induce formation of a helical array.

BACKGROUND OF THE INVENTION

Native collagen has a primary structure of repeating trimeric amino acid sequences. Within a helical region, which constitutes about 95% of the molecule, the amino acid glycine (Gly) occurs at every third position of a peptide trimer. Imino residues (I), either proline (Pro) and hydroxyproline (Hyp), occur in 56% of the trimers, 20% as Gly-X-I; 27% as Gly-I-Y; and 9% as Gly-I-I. Pro usually occurs in the second position in the repeating trimer; while Hyp usually occurs in the last position. (Bhatnagar, R. and R. Rapaka (1976) Chap. 10 in *Biochemistry of Collagen* R. Ramachandren, ed. Plenum Press, New York. pp.481–482).

Tripeptide sequences (Gly-X-Y) wherein X and Y are amino acid residues other than proline (Pro) or hydroxyproline (Hyp) make up 44% of the collagen amino acid trimers. Glutamic acid, leucine, and phenylalanine occur mostly in the X position and threonine, glutamine, methionine, arginine and lysine occur mostly at the Y position. With the exception of alanine and serine, the X position amino acids have bulky side chains.

Synthetic collagens are of interest because they provide materials for collagen-like biomaterials having diverse clinical applications, including use in drug delivery devices, ocular devices, and wound healing materials. Because the proline and hydroxyproline (a post-translationally modified proline residue) residues are abundant in natural collagen sequences, many sequential polymers composed of the trimeric amino acid sequences Gly-Pro-Xaa and Gly-Xaa-Pro (where Xaa is any natural amino acid residue) have been prepared to mimic the collagen structures. (Segal, D. M., and Traub, W.(1969) *J. Mol. Biol.* 43:487–496 disclose poly(L-alanyl-L-prolyl-glycine); Segal, D. (1969) J. Mol. Biol. 43:497–517) discloses collagen-like polyhexapeptides (Gly-Ala-Pro-Gly-Pro-Pro)$_n$, (Gly-Pro-Ala-Gly-Pro-Pro)$_n$, Gly-Ala-Pro-Gly-Pro-Ala)$_n$, and (Gly-Ala-Ala-Gly-Pro-Pro)$_n$; Sakakibara, S. (1973) Biochim. Biophys. Acta 303:198–202 discloses (Pro-Hyp-Gly)$_n$; Scatturin, A. (1975) Intl. J. Peptide Protein Res. 7:425–435 discloses (Pro-Leu-Gly)$_n$ and (Leu-Pro-Gly)$_n$; Bansal, M. (1978) Peptide Protein Res. 11:73–81 discloses (Gly-Pro-Leu)$_n$ and (Gly-Leu-Pro)$_n$; and Miller, M. (1980) Macromolecules 13:910–913) discloses poly(glycylprolylalanyl). Ananthanarayanan, V. et al. (1976) in Chap. 15, Biopolymers, pp. 707–716 (J. Wiley & Sons) disclose polymers wherein the triplet contains the isomeric N-methyl glycine sarcosine as (Gly-Pro-Sar)$_n$ and (Gly-Sar-Pro)$_n$. The publications cited above are incorporated by reference.

Collagen has a characteristic tertiary, secondary and primary structure. Most polypeptides comprise sequences of amino acids in peptide linkage which are arrayed either in an α-helix, a right-handed spiral, or alternatively, in a pleated sheet β-conformation. In each of these arrays the amino acids of neighboring polypeptide strands are held in place by intramolecular hydrogen bonds. Collagen, by comparison, is made up of three polypeptide chains comprising repeating amino acid trimers. These chains are arrayed in three extended left handed spirals of about three residues per turn, the polyproline II-like chains (Rich, A. et al. (1955) Nature 176:915). The polyproline II-like chains of collagen are arranged in a parallel direction and intertwined to adopt a supercoiled, or coiled coil, right-handed triple helix conformation (Bella, J. et al. (1994) Science 266:75–81) that is also characteristic of collagen. The chains that make up the collagen triple helix can be homotrimeric, that is, made up of identical repeating amino acid trimers, or they can be heterotrimeric, made up of chains of different amino acid trimers.

The association of polyproline II-like chains into a triple helix occurs spontaneously; however, the rate of helix formation may be slow because of the repulsive like charges at the amino and carboxyl ends of the polypeptide sequences that oppose an association of the chains. This "end effect" becomes less important as chain length increases. The rate of helix formation can also be slow because the amino acids in each chain must first line up, or be in "register" properly with each other, and to do so they must adjust position appropriately, one along the length of the other. Collagen chains have been found to require a one residue shift between corresponding amino acids in each chain in order to register properly and form trans amides for all peptide bonds.

Mimicry of natural collagen structures has been directed to enhancing their biostability by inserting unnatural residues into the peptide sequences. To enhance the biostability of collagen-like structures therefore, many unnatural proline analogs and other unnatural imino acid residues have been used to replace the frequently occurring proline residue in the peptide sequences. However, incorporation of such residues, such as the lower homologue of proline, azetidine-2-carboxylic acid (Aze), has been found to destabilize the triple helical structure of collagen or to prevent its formation (Zagari, A. et al. (1994) *Biopolymers*, 34:51–60).

Peptoid residues are a new class of unnatural imino acids (Simon, R. J. et al. (1992) Proc. Natl. Acad.Sci. USA 89:9367–9371) containing N-substituted glycine residues wherein the substituents on the nitrogen atom are the α-position side chains of amino acids. Because they are amino acids that do not occur in nature, peptoid residues or peptides containing peptoid residues have higher resistance to enzymatic attacks. In recent years, peptoid residues have been widely used in the design and synthesis of drugs and other peptide related biomaterials.

Template directed synthesis, the interaction of one molecule with an assembly of atoms to induce a preferred molecular architecture, is known in nature. The replication of DNA, for example, involves a templated synthesis of daughter polynucleotides from progenitor molecules having the same tertiary structure. A template-assembling approach has been widely used for the design and synthesis of protein analogs with high molecular weights. Molecular templates have been used in chemical synthesis to fix peptide loops and to induce the α-helix and β-turn structures of polypeptides. Kelly, T. R. et al. (1990) J. Amer. Chem. Soc. 112:8024–8034, have reported use of a linear template to form β-structures. Muller discloses anthracene-type tricyclic structures that can bridge two antiparallel peptide β-strands or induce β-turns. Muller also discloses that Kemp triacid condensed with glycine or alanine can act as a templates for inducing α-helicity of an attached polypeptide (Muller, K. et al. (1993) Chap. 33 in *Perspectives in Medicinal Chemistry*, B. Testa et al., eds, verlag, Basel). Ghadiri, M. et al. (1993) Angew. Chem. Int. Ed. Engl. 32:1594–1597 have prepared a polypeptide 3-α-helix bundle containing a ruthenium metal bipyridyl complex.

Roth, W. et al. (1980) Biopolymers 19:1909–1917 has used lysine dimers and 1,2,3-propane carboxylic acid to prepare covalently bridged synthetic collagen model peptides which were found to assemble into a triple helix. Fields, C. G. et al. (1993) Biopolymers 33:1695–1707 and Tanaka, T. et al. (1993) FEBS 13257 334(3) :272–276, have used two consecutively connected lysine residues with three functional amino groups to link three peptide chains at the C-termini or the N-termini. Fields et al. report the formation of thermally stable collagen-like polypeptide sequences in triple helical conformation by a solid phase procedure wherein three collagen-like peptide strands were synthesized in parallel from an origin at adjacent amine groups at the C-terminal. The branching of the peptide chains is reported to ensure the proper alignment or register of the chains in the triple helical polypeptide as they would be in native collagen.

In order to prepare synthetic collagen that has the properties of native collagen, the synthetic material must mimic collagen in tertiary as well as primary and secondary structure.

SUMMARY OF THE INVENTION

According to the invention there is provided a synthetic collagen-like material comprising chains of repeating trimeric amino acid building blocks, in which about 30% of the amino acids are glycine, and at least about 10% are proline or hydroxyproline, the improvement comprising the incorporation, at least in part, of peptoid residues in said repeating trimeric building blocks and formation of a peptoid residue-containing triple helix from the chains assembled from those peptoid residue containing building blocks. In a preferred embodiment, the synthetic collagen-like material comprises chains of repeating trimeric building blocks in which the trimeric sequences are made up of a peptoid residue and two amino acid residues. In a particularly preferred embodiment 30% of the residues of the trimeric sequences are glycine amino acid residues, and at least about 10% are proline or hydroxyproline amino acid residues, and at least 10% are peptoid residues. These trimeric sequences, each made up of two amino acid residues and one peptoid residue, are incorporated in peptoid residue-containing amino acid chains which are then formed into a peptoid residue-containing triple helix.

In a preferred embodiment of this aspect of the invention the synthetic collagen material comprises chains of repeating building blocks which are either tripeptide sequences, trimeric dipeptide-peptoid residue sequences or peptide-peptoid residue-peptide sequences selected from the group consisting of Gly-Xp-Pro; Gly-Pro-Yp; Gly-Pro-Hyp; and Gly-Pro-Pro; or combinations thereof, wherein Xp and Yp are peptoid residues, and the chains have a triple helix conformation similar to that of collagen. In a particularly preferred embodiment, the synthetic collagen material comprises amino acid chains made up of repeating trimeric building blocks selected from the group consisting of Gly-Xp-Pro and Gly-Pro-Yp; or combinations thereof. Optionally, the chains can comprise Gly-Pro-Pro and Gly-Pro-Hyp trimers.

The invention includes amino acid chains having terminal blocking groups, wherein the chains have the formula

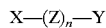

and comprise at least one dipeptide-peptoid residue trimer, Z, selected from the group consisting of (Gly-Xp-Pro)$_j$; and (Gly-Pro-Yp)$_k$-, wherein Xp and Yp are peptoid residues; and optionally at least one tripeptide selected from the group consisting of (Gly-Pro-Pro)$_x$; and (Gly-Pro-Hyp)$_m$;

and the sum of j, k, l and m in said amino acid chain is n, and n is ≧3; wherein X is selected from the group consisting of linear, branched, saturated or unsaturated aliphatic acids, aromatic carboxylic acids, and aralkyl carboxylic acids and is linked to the N-terminal amino acid of the polypeptide by an amido linkage; and wherein Y is selected from the group consisting of ammonia, linear, branched, saturated or unsaturated aliphatic amines, aromatic amines, and aralkyl amines and Y is linked to the C-terminal end of the polypeptide by an amido linkage.

In the peptoid residue-containing synthetic collagen materials of the invention, the peptoid residue of the repeating trimeric sequence is selected from the group consisting of N-substituted peptoid isomers of glycine, valine, leucine, isoleucine, glutamine, lysine, phenylalanine, and aspartic acid residues. For example, the repeating peptoid-residue containing triplet is of the formula Gly-Pro-Nleu or Gly-Nleu-Pro.

The invention also includes amino acid chains comprising repeating Gly-Pro-Hyp trimeric sequences or the amino acid chains comprising repeating trimeric sequences containing peptoid residues wherein the repulsive charges on the ends of the chains that oppose helicity are removed by acetylation at the N-terminal and amidation at the C-terminal.

The invention also provides template-bound amino acid chains of repeating peptide-peptoid residue trimers of the formula TP-[A-(Gly-Xp-Pro)$_n$—NH$_2$]$_3$, TP-[A-(Gly-Pro-Yp)$_n$—NH$_2$]$_3$ or combinations thereof, wherein TP is a template molecule capable of inducing triple helical folding of the polypeptide chains, having three regularly spaced functional groups, each of which groups is covalently bound to a repeating peptide-peptoid residue chain; A is an optional multifunctional spacer molecule; Xp and Yp are peptoid residues; and n≧3.

According to one embodiment of this aspect of the invention there are provided template-bound polymers of repeating peptide trimers of the formula TP-[A-(Gly-Pro-Hyp)$_n$—NH$_2$]$_3$. The amino acid chains attached to the templates can comprise combinations of tripeptides and trimeric sequences made up of a peptoid residue and two peptide residues.

According to a related embodiment there is provided a template-bound amino acid chain assembly comprising: a template molecule, TP, with three regularly spaced functional groups; an optional spacer, A, comprising a $C_1$ to $C_6$ alkyl chain with functional end groups; three amino acid chains comprising repeating trimeric peptide sequences or trimeric sequences in which a peptoid residue is substituted for a peptide or mixtures of the described trimeric sequences selected from the group consisting of (Gly-Xp-Pro)$_j$; (Gly-Pro-Yp)$_k$-; (Gly-Pro-Pro)$_l$; and (Gly-Pro-Hyp)$_m$ wherein Xp and Yp are peptoid residues; j, k, l and m are each 0-n; and the sum of j+k+l+m=n, wherein n is ≧3, wherein the amino acid chains have the same or different amino acid sequences and are covalently bound to the functional groups of said template molecule directly or through the spacer, A; and the template molecule induces triple helical folding of the chains.

In preferred embodiments of this aspect of the invention the template molecule is the Kemp triacid (KTA) (cis,cis-1,3,5-trimethylcyclohexane-1,3,5-tricarboxylic acid), or trimesic acid (TMA) (1,3,5-benzenetricarboxylic acid); A is a spacer selected from the group consisting of Gly (—NH—CH$_2$—COO—) and 6-aminohexanoic acid (—NH$_2$—(CH$_2$)$_5$—COO—); and Xp and Yp are selected from the group consisting of Nleu (add other peptoids).

In particular embodiments of this aspect of the invention, there are provided template-bound amino acid chains of the formula KTA-(Gly-(Gly-Pro-Yp)$_n$—NH$_2$)$_3$;
KTA-(Gly-(Gly-Xp-Hyp)$_n$—NH$_2$)$_3$;
KTA-(Aha-(Gly-Pro-Yp)$_n$—NH$_2$)$_3$; or
KTA-(Aha-(Gly-Xp-Hyp)$_n$—NH$_2$)$_3$ wherein Yp and Xp are peptoid residues; KTA is Kemp triacid (cis,cis-1,3,5-trimethylcyclohexane-1,3,5-tricarboxylic acid); Aha is 6-aminohexanoic acid (—NH$_2$—(CH$_2$)$_5$—COO—); and n is $\geq 1$.

There are also provided template bound amino acid chains of the formulas

TMA-(Gly-(Gly-Pro-Yp)$_n$—NH$_2$)$_3$; or
TMA-(Gly-(Gly-Xp-Hyp)$_n$—NH$_2$)$_3$;

wherein Xp and Yp are peptoid residues; TMA is trimesic acid (1,3,5-benzenetricarboxylic acid); and n is $\geq 1$ In preferred embodiments of the template-bound assembly of the invention, Xp is selected from the group consisting of N-substituted glycines and other peptoid residues.

The invention also provides a process for inducing triple helical folding of three amino acid chains comprising the steps of (a) covalently attaching the N-terminus of one amino acid chain to each of three functional groups of a helix-inducing template molecule, either directly or through a multifunctional spacer molecule; (b) permitting the template-assembled amino acid chains to assume a stable triple helical conformation.

One embodiment of this aspect of the invention comprises a preliminary step of assembling the three amino acid chains by a solid phase segment condensation method on a resin support. An associated process comprises attaching the N-termini of resin-bound assembled amino acid chains to the functional groups of the template, optionally through a spacer linked to the template. Alternatively, amino acids are released from the resin following assembly and the N-termini of assembled free amino acid chains are then attached to the functional groups of the template molecule in solution. In preferred embodiments of any of the template assembly processes described, the amino acid chains can comprise trimeric sequences selected from the group consisting of Gly-Xp-Pro; Gly-Pro-Yp; Gly-Pro-Hyp; and Gly-Pro-Pro; or combinations thereof, wherein Xp and Yp are peptoid residues. Helically arrayed collagen-like polymers according to the invention can also comprise amino acid chains of repeating trimeric sequences of the formula (Gly-Xp-Pro)$_n$-; or (Gly-Pro-Yp)$_n$ or combinations thereof, wherein Xp and Yp are peptoid residues, and n$\geq$3. Similarly, the collagen-like polymers can comprise repeating peptide trimers. In particularly preferred embodiments, the repeating peptide trimers are selected from the group consisting of Gly-Pro-Hyp, Gly-Pro-Pro or combinations thereof.

The invention further provides synthetic collagen materials comprising the helically arrayed three amino acid chains prepared by the processes disclosed.

BRIEF DESCRIPTION OF THE DRAWINGS

FIG. 1 depicts the Kemp Triacid template structure:

FIG. 1(a) shows the Kemp Triacid molecule in a chair conformation in which its three carboxyl functional groups, can be coupled to the N-termini of the three amino acid chains;

FIG. 1(b) shows three amino acid chains of the repeated sequence (Gly-Pro-Hyp)$_3$ attached to the three carboxyl functional groups of a Kemp triacid molecule through glycyl spacers. The purity of the final KTAg-3,3: (Kemp triacid-(Gly-(Gly-Pro-Hyp)$_3$)$_3$)$_3$) product as confirmed by a homogeneous single peak profile on analytical RP-HPLC.

DETAILED DESCRIPTION OF THE PREFERRED EMBODIMENTS

Figure 2:
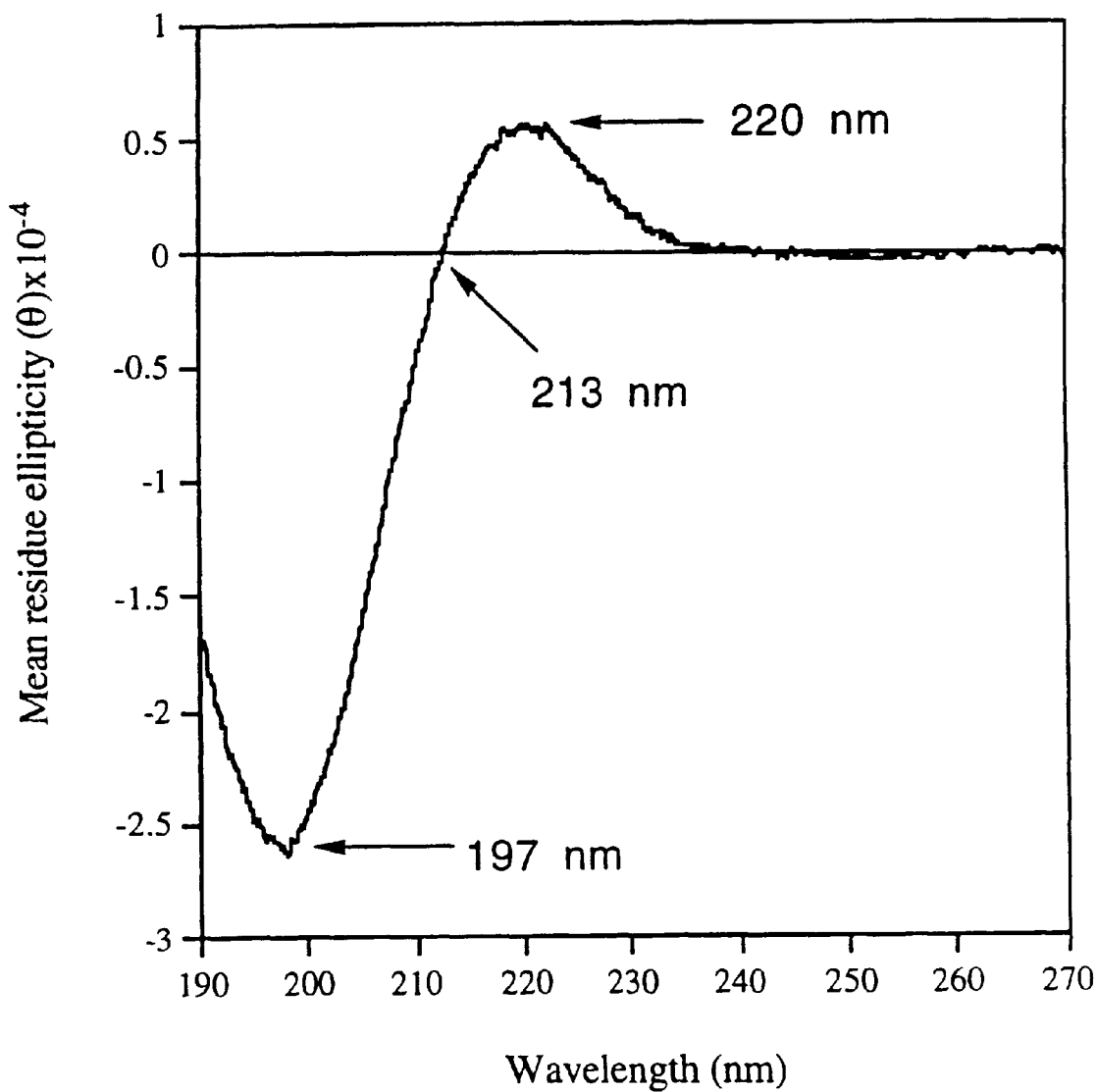
FIG. 2 is a circular dicroism (CD) spectrum of the repeated dipeptide-peptoid residue sequence Ac-(Gly-Pro-Nleu)$_9$—NH$_2$ in water at 20° C., 0.2 mg/ml.
Figure 3:
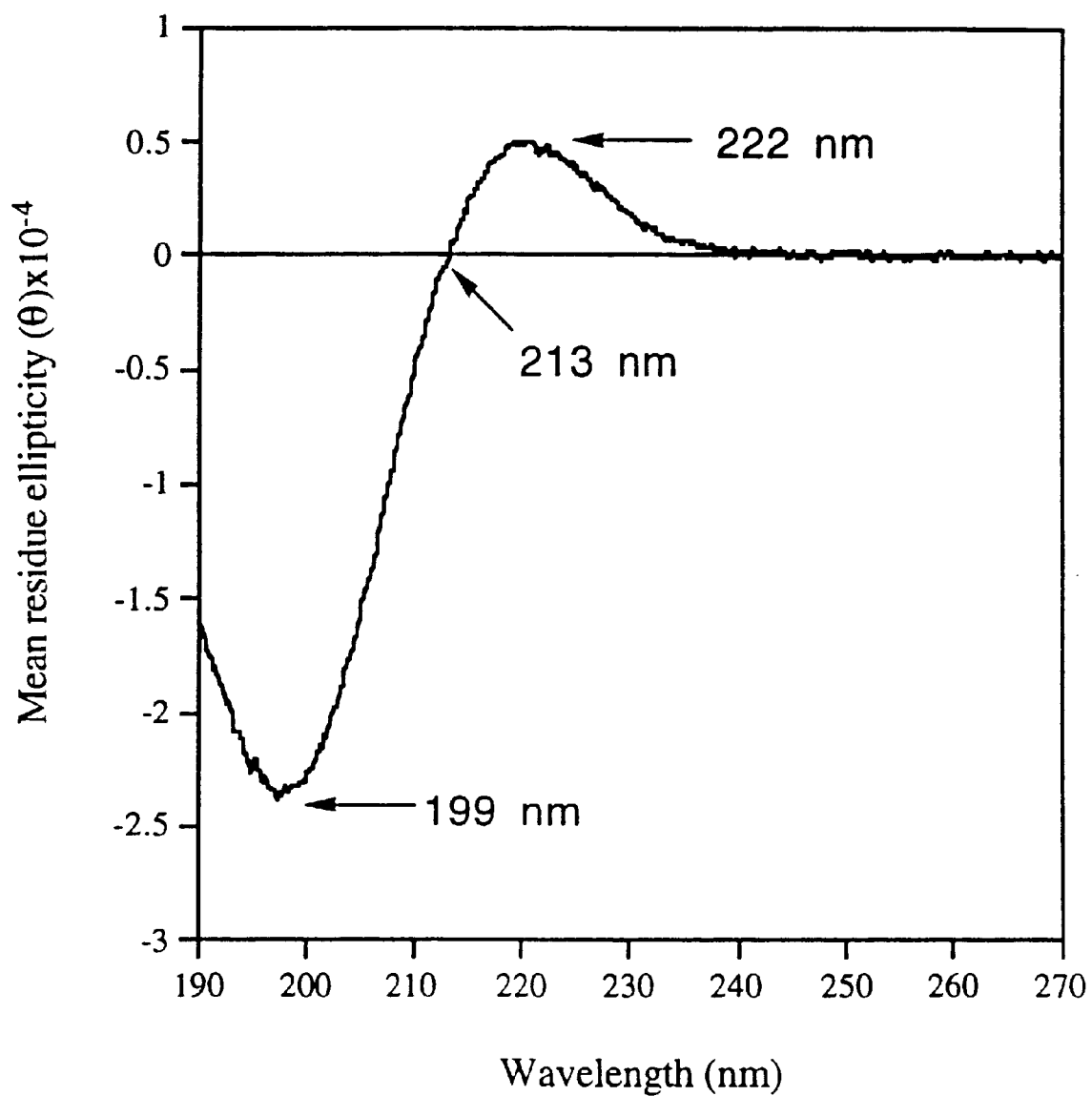
FIG. 3 is a circular dicroism (CD) spectrum of template-bound repeated dipeptide-peptoid residue sequences KTA-[Gly-(Gly-Pro-Nleu)$_6$—NH$_2$]$_3$.

I. General
  A. Terminology
  B. Overall Description of the Invention
II. Polymers of Peptide-peptoid Residue Trimers
  A. Repeating Trimer Building Blocks
  B. Single Chain Polymers of Trimers
III. Collagen-like Triple-helices
IV. Helix-inducing Templates
V. Conformational Analysis
VI. EXAMPLES
  A. Single Chain Structures
  B. Template-assembled Structures

I-A. Terminology

The following frequently used terms and abbreviations are intended to have the following meaning:

collagen-like A structure comprising α-amino acids arranged in a triple helix of polypeptide chains characteristic of collagen. Each polypeptide chain has the secondary structure of a right-handed spiral, the polyproline II-like chains; and the three chains are coiled in a left-handed helical array.

Kemp triacid (KTA) (cis,cis-1,3,5-trimethylcyclohexane-1,3,5-tricarboxylic acid)

monodisperse for polymers and biopolymers, refers to structures made up of single molecules of the uniform size or sequences of the same length and having a uniform molecular weight.

polydisperse for polymers and biopolymers, refers to polymerized monomers or suitable building blocks. In the polymerization process, chain elongation leads to polymers with different chain lengths. The polymer molecules are said to be polydisperse, that is having a distribution of sizes or lengths and molecular weights.

peptide or peptide residue A member of an oligomer of amino acids attached to each other by peptide bonds.

peptoid residue An isomeric N-substituted glycine, wherein the side chain of an α-amino acid is attached to the amino nitrogen instead of to the α-carbon of that molecule, as a member of an oligomer of amino acids attached to each other by peptide bonds.

Examples of Particular Peptoid Monomers are:

Sar: N-methyl glycine

Nval: N-isopropyl glycine

Nleu: N-isobutyl glycine

Nile: N-sec-butyl glycine

Nglu; Nlys; Nphe; Nasp: the peptoid residues related to glutamine, lysine phenylalanine and aspartic acid, respectively.

peptoids Oligomers or polymers of N-substituted glycines.

polyproline II-like The characteristic helical conformation of a single chain collagen polypeptide comprising a left-handed extended helical coil. In polyproline II, the peptide bonds have a trans conformation.

register The alignment of amino acids of neighboring collagen polypeptide chains favorable to intrachain hydrogen bonding.

Rpn An index of triple helicity which is the ratio of the intensity of the positive and negative peaks of the circular dicroism spectrum of a collagen-like assembly.

spacers Multifunctional molecules that connect the template molecule through its functional groups to the synthetic collagen chains. Examples: Gly: glycine (—NH—$CH_2$—COO—) and Aha: 6-aminohexanoic acid (—$NH_2$—$(CH_2)_5$—COO—).

TASP Template-Assembled Synthetic Proteins are artificial proteins having a predetermined three-dimensional structure formed by a process of fixing secondary-structure-forming peptide blocks on a tailor-made template molecule which directs the peptides into a packing arrangement.

template a molecular tool, typically a multifunctional molecule, that can direct the formation of a preferred molecular architecture or organization from attached chains that have the potential to assemble in a number of ways, including ordered helical arrays.

trimeric building blocks of collagen Repeating trimeric sequences wherein each monomer of the trimer is either a peptide residue or a peptoid residue. Also referred to as trimer or trimeric repeats. The trimer sequence can be a tripeptide, a dipeptide attached to a peptoid residue, or a peptide-peptoid-peptide residue sequence.

trimesic acid (TMA) (1,3,5-benzenetricarboxylic acid)

I-B. Overall Description of the Invention

It has been discovered that the substitution of peptoid residues in repeating amino acid trimers of collagen chains can provide collagen-like materials having improved properties. This invention includes use of peptide-peptoid residue trimers as building blocks to form novel collagen-like structures. Of course, it also includes co(peptide-peptoid residue) sequences specifically placed as building blocks in the collagen-like structures that include tripeptide building blocks.

The peptoid residue content of the collagen-like material can be minimal. Alternatively, peptoid residues can replace all of the proline and hydroxyproline in a typical collagen amino acid composition. For example, the collagen-like material can comprise at least about 30% glycine; and at least about 10% peptoid residue substituted for proline or hydroxyproline. Remaining amino acids can those that occur in native collagen as described in Bhatnagar, R. and R. Rapaka, cited above. Materials of the invention can also include collagen-like material wherein a peptoid residue occurs in every amino acid triplet. It has further been discovered that the use of helix-inducing templates can aid in assembling collagen-like polytripeptides and poly (peptide-peptoid residues) into a triple helical conformation characteristic of natural collagen. In any particular case, triple helix formation can be demonstrated as in the Examples.

II. Polymers of Peptide-peptoid Residue Trimers

A. Repeatinq Trimer Building Blocks

Previous studies indicate that incorporation of many types of proline analogs and other unnatural imino acids into single chain collagen-like amino acid sequences interferes with the formation of collagen triple helical structures. In an approach to mimic the collagen-like structures more closely, according to one embodiment of the invention, a peptoid residue was used as the proline surrogate in collagen-like repeated amino acid trimers.

Peptoid residues are N-substituted glycines, wherein the side chain of an amino acid has been moved from the α-carbon to the α-nitrogen. These isomers of amino acids are named as N-amino acids, that is, as Nleu, Nval, and Nlys for example. Preferred peptoid residues for use in the invention are those wherein the N-substituents are the hydrophobic non-polar side-chain groups of the amino acids or their analogues, for example the isopropyl group of valine (Nval), the isobutyl groups of leucine (Nleu) or isoleucine (Nile), the propyl group of norvaline, the butyl group of norleucine. Other useful peptoid residues are N-glutamic acid (Nglu), N-lysine (Nlys). In an exemplification of the invention, a peptoid residue, N-isobutylglycine (Nleu), was used as a proline surrogate.

Although the invention is not limited to peptoid residues having the side chains of natural amino acids, collagen-like polymers comprising N-substituted peptoid residues having side-chain groupings that are similar to peptide residues are comparable to native collagen sequences and are believed to be more compatible with natural proteins than other unnatural imino acid residues. Biophysical and biochemical studies indicate that unlike other proline analogs and unnatural imino acids, such peptoid residues, when incorporated into collagen-like sequences, are indeed compatible with collagen triple helical structures. According to the invention, however, substituents attached to the nitrogen of the peptoid residues can be any group, for example, an aromatic or aralkyl group or a linear or branched alkyl group of at least 2 carbon atoms. The substituents can also be hydrophilic or hydrophobic, and may comprise functional groups.

However, the incorporation of N-methyl glycine (sarcosine) wherein the N-substitutent, the methyl group of alanine, is the least hydrophobic and least bulky amino acid side group, does not provide a peptoid residue-containing chain that assembles satisfactorily into a triple helix.

The synthesis of a peptoid residue, for example, N-substituted glycine, involves the displacement of an amino proton of glycine by an α-position side chain, preferably the side chain of a natural amino acids. The reaction can be carried out in solution by several synthetic routes, for example, reductive amination of a side chain amine with glyoxylic acid as disclosed by Rogers, T. et al. (1986) Chem. Abstr. 105:226986z; or as disclosed by Buckus, P. (1964) Chem. Abstr. 61:5511b, alkylation of a side chain with haloacetic acid or, for the Ngln peptoid residue (related to glutamine). Michael addition of glycine to acrylamide has been used. The solid phase condensation of a haloacetic acid and a primary amine according to Zuckerman, R. N. et al. (1992) J. Amer. Chem. Soc. 114:10646–10647 or Sakakibara, S. et al. (1973) *Biochim. Biophys. Acta* 303:198–202 is preferred.

Peptoid residues of the N-substituted glycine structure according to the invention are accordingly prepared by the alkylation of an alkyl- or isoalkylamine with ethyl bromoacetate. These peptoid residues are also prepared by reductive amination of C-terminal protected glycine with an alkylaldehyde. Synthesis of the peptoid residues by the alkylation and reductive amination methods is exemplified in Example 4. Both routes give high yields.

The single-chain structures which can form collagen-like structures according to one aspect of the invention are composed of polymers of collagen-like tripeptides each of which includes one peptoid residue. Preferred peptide-peptoid residue trimers have the formula Gly-Xp-Pro or Gly-Pro-Yp wherein Xp and Yp are peptoid residues. These trimeric building blocks are prepared by coupling terminal protected amino acids and peptoid residues in solution using a stepwise method.

To obtain the preferred dimer Boc-Gly-Pro-OH (Boc:t-butyloxycarbonyl), the p-nitrophenol active ester Boc-Gly-ONp is prepared first and then allowed to react with proline in dimethylformamide (DMF) with a small amount of water, using triethylamine (TEA) as the catalyst. The N-alkylglycine ester (Yp-OEt) is coupled to this dipeptide-free acid in DMF with 1-ethyl-3-(3-dimethylaminopropyl)-carbodiimide (EDC) and N-hydrobenzotriazol (HOEt) as the coupling reagents to obtain the tri(peptide-peptoid residue) Boc-Gly-Pro-Yp-OEt. The terminal ethyl group is removed by hydrolysis to obtain the building block tripeptoid-free acid Boc-Gly-Pro-Yp-OH. The Gly-Xp-Pro peptide-peptoid species is prepared in a similar manner.

To obtain the preferred dimer Boc-Gly-Xp-OEt, Boc-Gly-OH is also coupled to Xp-OEt in DMF using benzotriazolyloxytris (dimethylamino)phosphonium-hexafluorophosphate (BOP) as the coupling reagent. After hydrolysis, the resulting dipeptide free acid Boc-Gly-Xp-OH is coupled to Pro-OBz using EDC and HOBt as the cooling reagents to obtain the peptoid residue-containing trimer Boc-Gly-Xp-Pro-OBz. Then, the benzyl protective group is removed by hydrogenation using Pd/C as the catalyst to obtain the trimeric building block Boc-Gly-Xp-Pro-OH. All the preferred trimer products (Gly-Pro-Yp-$NH_2$, Ac-Gly-Pro-Yp-$NH_2$, Ac-Gly-Pro-Yp-$NHCH_3$Gly-Xp-Pro-$NH_2$, Ac-Gly-Xp-Pro-$NHCH_3$) and (Gly-Pro-Yp)$_2$—$NH_2$ can be prepared by peptide synthesis methods in solution.

The synthesis of the trimeric building blocks containing a peptoid residue is set forth in Examples 5 and 6.

II-B. Single Chain Polymers of Trimeric Peptoid Residue-containing Building Blocks Collagen-like chains comprising building blocks of repeating trimeric peptoid residue-containing sequences have been prepared. Among the embodiments according to this aspect of the invention are preferred single chains that can form collagen analogs composed of the Gly-Pro-Nleu and Gly-Nleu-Pro repeating sequences incorporating the Nleu peptoid residue. Monodisperse sequences of trimers containing the peptoid residue were prepared in order to compare the triple helical propensities of the monodisperse sequences having triplet repeats less than 10, composed of the Gly-Pro-Nleu or Gly-Nleu-Pro sequences with that of (Gly-Pro-Leu)$_{10}$ which has already been shown to be unable to form collagen-like triple helical arrays under all conditions attempted (Scatturin, A. et al. (1975) Int. J. Peptide and Protein Research 7:425–435). This comparison demonstrates the advantage of the peptoid residues over amino acid residues in triple helix formation.

A solid phase segment condensation approach based on the method introduced by Sakakibara et al., using a 4-methylbenzhydryl-amine (MBHA) resin, was employed to prepare the single chain collagen-like sequences of the examples.

Corresponding sequences containing, for example, peptoid residues Nglu, Nlys, Nphe, Nval, Nasp and Sar have been prepared, and these peptoid residues can also be inserted into the trimer sequence Gly-Pro-Xaa or Gly-Xaa-Pro.

The trimeric building blocks Boc-Gly-Pro-Yp-OH and Boc-Gly-Xp-Pro-OH can be synthesized in solution by standard peptide stepwise coupling. A solution segment condensation method was used to prepare (Gly-Pro-Yp)$_2$—$NH_2$. Boc-Gly-Pro-Yp-OH was coupled to Gly-Pro-Yp-$NH_2$ in DMF using BOP as the coupling reagent to get Boc-(Gly-Pro-Yp)$_2$—$NH_2$. Then, the Boc group was removed to obtain the N-terminal free amine trimer (Gly-Pro-Yp)$_2$—$NH_2$. All these small trimeric sequences prepared in solution were also purified by RP-HPLC.

The coupling reagents used in the solid phase synthesis included diisopropylcarbodiimide (DIC) and HOBt; the solvent used in coupling reactions was 25% DMF in DCM. A solution of TFA in DCM (30%) was used to remove the Boc group after each coupling, and a solution of 10% TEA in DCM was used for neutralization. The Kaiser ninhydrin test was used to monitor each coupling reaction. From 1.2 to 1.5 equivalents of the preferred building block trimer Boc-Gly-Pro-Yp-OH were used together with about 2 equivalents of the coupling reagents DIC and HOBt at each coupling, and the peptide bond formation normally took 4–8 hours.

The synthesis and characterization of other sequences with repeating trimeric building blocks Ala-Sar-Gly, Gly-Sar-Ala, Ala-Nphe-Gly, Glu-Sar-Gly, Lys-Sar-Gly and Gly-Pro-Sar are also reported in Goodman, M. et al. (1994) Polymer Preprints 35(1):767–768.

III. Collagen-like Triple Helices

Natural collagen and collagen-like polytripeptide sequences in the N-terminal free amine and C-terminal free acid are able spontaneously to adopt a triple helical conformation when the chains are very long. However, for limited chain length analogs, cation formation on the N-termini and anion formation on the C-termini can introduce negative "end effects" that induce repulsive forces between chains and interfere with helix formation. For example, (Gly-Pro-Hyp)$_{10}$—OH spontaneously adopts a triple helix conformation at room temperature (Venugopal, M. et al. (1994) Biochemistry 33:7948–7956); however (Gly-Pro-Hyp)$_5$ does not maintain helicity above 5° C. Helix formation of shorter chains can be accomplished by N-terminal acetylation and C-terminal amidation which removes the described end effects.

A suitable N-terminal acetylating agent is any molecule having a carboxyl group available for binding the terminal amine. Preferred agents are linear, branched, saturated or unsaturated aliphatic acids, aromatic carboxylic acids, and aralkyl carboxylic acids. A suitable C-amidation agent is any molecule having an amine group available for binding the terminal carboxyl of the chain. Preferred agents are ammonia, linear, branched, saturated or unsaturated aliphatic amines, aromatic amines, and aralkyl amines. Non-limiting examples of suitable C-terminal groups are amide, bipyridine, and maleimide.

To synthesize the C-terminal amide compounds, $NH_4Cl$ and HCl. $NH_2CH_3$ were used with triethylamine to produce the amines $NH_3$ and $NH_2CH_3$, which in turn were allowed to react with Boc-Gly-Pro-Yp-OH or Boc-Gly-Xp-Pro-OH simultaneously to obtain the N-terminal Boc-protected trimeric peptoid residue-containing amide compounds. The Boc group was then removed using a solution of 30% TFA in DCM. HCl/dioxane (4N) was used to obtain the products as hydrogen chloride salts. To obtain the C-terminal amide compounds in solid phase, 4-methylbenzylamine resin (MBHA, 200–400 mesh, 1% DVB, 0.45 mmol/g), which yields an amide on the peptide C-terminal after the HF cleavage, was employed.

To prepare the acetyl compounds, acetic anhydride was used to acetylate the N-termini of the trimeric peptoid residue-containing amide compounds in DCM with triethylamine as the base. The preparation of these products is set forth in Example 8.

To prepare the acetyl compounds in solid phase, the Boc group was removed and acetic anhydride in DCM with about 5% TEA was used to acetylate the N-termini of the peptide chains after the expected chain length is reached. The acetylation took 30–60 minutes. The following compounds were prepared by this solid phase segment condensation method: $(Gly\text{-}Pro\text{-}Nleu)_n$, —$NH_2$ (n=1,2,3,4,5,6,7,9), Ac-$(Gly\text{-}Pro\text{-}Nleu)_n$, —$NH_2$ (n=1,6,9), $(Gly\text{-}Nleu\text{-}Pro)_9$—$NH_2$ (n=1,9), Ac-$(Gly\text{-}Nleu\text{-}Pro)_n$, —$NH_2$ (n=3,6,10) and Ac-$(Gly\text{-}Pro\text{-}Sar)_{10}$-Gly-OH. The synthesis of the single chain collagen analogs of the invention is outlined in Schemes 4–5 and exemplified in Examples 7 and 8.

The efficacy of N-terminal acetylation of single chains can be demonstrated by comparing the melting temperatures of $(Gly\text{-}Pro\text{-}Hyp)_5$, (5° C. in 50% ethanol/water), and Ac-$(Gly\text{-}Pro\text{-}Hyp)_5$—$NH_2$, 23° C. in 50% ethanol/water). Accordingly, embodiments of this aspect of the invention include N-terminal acetylated single chain polypeptides of the general formula Ac-n, wherein n represents the number of repeating collagen-like trimers. Preferred members of this group are collagen chains of the formulas Ac-$(Gly\text{-}Pro\text{-}Hyp)_n$—$NH_2$, Ac-$(Gly\text{-}Xp\text{-}Hyp)_n$ or Ac-$(Gly\text{-}Hyp\text{-}Yp)_n$.

IV. Helix-inducing Templates

Because the triple helical structures of native collagen involve three parallel polyproline II-like chains intertwined to form a super-helix, a template with three functional groups to connect the three chains covalently or non-covalently at the same end (C-terminus or N-terminus) of the peptide chains is believed to be a feasible route to nucleate and propagate collagen triple helix formation.

Accordingly, a second type of collagen-like peptoid residue-containing structure according to the invention is based on analogs with terminal templates which induce triple helical conformations in these poly(peptide-peptoid residue) chains. In the template method, a template with functional groups is used to help the formation of a specific protein (or polypeptide) conformation. Templates have been used as part of a process termed Template-assembled-Synthetic-Protein (TASP:Tuchscherer, G. and Mutter, M. (1995) Journ. Peptide Sci. 1:3–10) to mimic the α-helix and β-turn structures of polypeptides, but have not been used previously to mimic collagen-like triple helical conformations. Two types of templates were used in a preferred approach according to the invention. One is based on derivatives of the Kemp triacid (KTA), a cyclohexane derivative which has three carboxyl functional groups all in the axial positions (Kemp, D. and K. Petrakis (1981) J. Org. Chem. 46:5140–5143). The second is based on derivatives of the trimesic acid (TMA) which has three carboxyl functional groups oriented in the plane of the benzene ring. The two templates have the following structures:

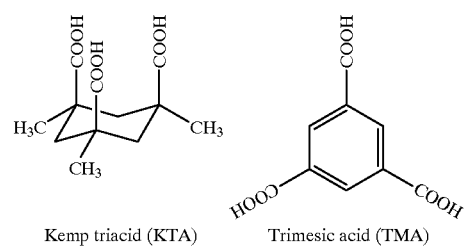

Kemp triacid (KTA)    Trimesic acid (TMA)

Highly constrained trifunctional molecular templates such as the Kemp triacid and trimesic acid have not previously been used to induce collagen-like triple helical formations among monodisperse collagen-like chains. It has been found that these templates dramatically facilitate collagen triple helix formation and stabilize the triple helical conformations for both collagen-like polytripeptides and poly(peptide-peptoid residues).

The highly constrained templates of the invention are believed to be superior to the highly flexible templates based on lysine dipeptides and other bridge structures of Roth (1980) and Fields (1993), cited above. The highly constrained templates of the invention, while holding the chains in parallel, can by means of the bending and flexing of the molecule frame, allow the residues of those chains to seek optimal register by movement along a path. The templates of Roth and Fields, by contrast, promote register of the chains by adjusting the alignment of each chain to another with a single residue increment shift.

Non-limiting examples of other trifunctional templates that are suitable, (although somewhat more flexible), for inducing collagen triple helix formation among collagen-like polypeptides or peptoid residue-containing chains of the invention are α-cyclodextrin, and aminotrithiol compounds. Functionalized molecules having the structures of fused cyclohexanes, condensed aromatics, adamantane, or steroids are suitable as helix-inducing templates according to the invention. Those skilled in the art can identify other suitable template structures.

The KTA templates are preferred as more compatible with collagen triple helical conformations because the three functional groups of the triacid can be coupled to the three peptide chains in collagen triple helical structures. The Kemp triacid KTA (cis, cis-1,3,5-trimethylcyclohexane-1,3,5-tricarboxylic acid), a conformationally constrained organic structure, was accordingly used as a template to nucleate the triple helical folding of three polypeptide chains containing (Gly-Pro-Hyp) triplet repeats.

Previous NMR studies indicate that KTA prefers a chair conformation in which the three carboxyl functional groups are in the axial positions. In this conformation the separation between the three axial carbonyl carbon atoms is 2.5–3.5 Å (Kemp, D. and K. Petrakis, 1981), while the distances between symmetry-related carbonyl carbon atoms bound to the Gly-NH in triple helical sequences are always greater than 4. To compensate for this difference in diameter and spacing, a spacer, for example, a glycine residue, can be inserted between each peptide chain and each carboxyl group on the template molecule, in this example KTA. The three polypeptide or peptoid residue-containing chains are therefore preferably linked to the templates through spacer molecules; glycine residues that act as spacers are preferred. A spacer junction between the template and the helix strands serves the purpose that it relieves steric hindrance among the chains. Also, in the supercoiled structure of the triple helix, the three chains are shifted by one residue. For example, in the Gly-Pro-Hyp sequence, at any given level the triple helix packing involves a Gly from one chain, a Pro from a second chain and a Hyp from a third chain. Because the spacer can twist and stretch to different conformations, the three peptide chains can adopt the proper shift necessary for the collagen-like triple helix array. Accordingly, when each carboxyl group of a Kemp triacid or trimesic acid is coupled to a strand of the triple helix through a flexible spacer such as glycine, the assembly allows for the proper shift and helical register.

To prepare the helix-inducing templates, the C-terminal benzylester-protected spacer residues (Gly-OBz, Aha-OBz) were first coupled to KTA and TMA in DMF by using EDC and HOBt as the coupling reagents. The C-terminal benzyl groups were removed by hydrogenation in methanol using Pd/C as the catalyst to produce the preferred templates with three carboxyl groups: KTA-(Gly-OH)$_3$, KTA-(Aha-OH)$_3$ and TMA-(Gly-OH)$_3$. The purity of these templates were checked by analytical HPLC profiles, and if necessary, they were further purified by performing preparatory RP-HPLC.

Two methods were used to attach the templates with carboxyl functional groups to the N-termini of peptide chains. In one of the preferred methods, the peptide-peptoid residue chains were assembled first on the resin. After a specific chain length was reached, the template was coupled to the N-termini by using DIC and HOBt as the coupling reagents. The product was removed from the resin by the HF cleavage method and purified by HPLC. This method was successfully used in the preparation of template-assembled collagen-like polypeptides composed of Gly-Pro-Hyp sequences. Some of the preferred template-assembled collagen-like polypeptide-peptoid residue trimers composed of Gly-Pro-Yp and Gly-Xp-Pro sequences were also prepared by this method.

According to another preferred method of the invention, the templates and the peptide chains were connected through a peptide bond formation in solution. The peptide-peptoid residue chains were assembled by the solid phase synthesis method and were cleaved from the resin as N-terminal free amines. These peptoid residue chains were purified by HPLC. The templates and the free-amine peptide-peptoid residue chains were coupled in solution using EDC and HOBt. This method was used in the preparation of several target template-assembled repeated trimeric building blocks, which optionally contained peptoid residues.

Innovative Collagen Template Design

The innovative design of collagen templates according to the invention is based on the observation that the KTA template is skewed compared to the triple helix axis as shown by molecular mechanics simulations. This observation has two important consequences which are relevant for the general design rationale of collagen triple helix templates.

First, the skewing mentioned above allows the template to adapt to the collagen triple helix register shift without any significant distortion of its geometry, as indicated by the KTA methylene chemical shifts which are very sensitive to conformational changes (Kemp, D. et al. 1981 J. Org. Chem. 46:5140–5143). The template can therefore be highly constrained without the risk of significantly distorting the triple helical array. This means that the free energy gain in the collagen triple helix formation obtained by highly constrained templates with proper spacers is greater than that allowed by the highly flexible templates published so far (Roth, W. et al. 1980 Biopol., 19:1909–1917; Fields, C. G. et al. 1993 Biopol., 33:1695–1707; Tanaka, T. et al. 1993, FEBS, 334 (3) :272–276). The increased free energy gain results from a better optimization of the entropy loss allowed by the highly constrained nature of the template, which at the same time does not lead to any significant enthalpy change.

Second, the skewing of the template as compared to the triple helix axis eliminates the requirement that the highly constrained templates have a ternary screw symmetry with the correct triple helix chirality. The collagen triple helix will instead induce the correct symmetry and transfer chirality to the template, as shown by modeling studies and by the splitting of the KTA signals in the NMR spectra acquired in conditions under which the triple helix is present. The highly constrained templates can therefore be achiral and have ternary rotational symmetry. This design rationale leads to target molecules which are more easily accessible by chemical synthesis than the chiral templates with screw symmetry.

The compound TMA-[(Gly-Pro-Nleu)$_9$—HN$_2$]$_3$ represents a molecule which does not possess any spacer residues between the template (TMA) and the peptide chains. This compound was prepared to show the necessity of spacers and a preferred conformation of the template with respect to the triple helix formation, especially when the peptide chains are long enough to compensate for the structural effects of an unpreferred template. To synthesize this compound, the TMA was activated to the acid chloride and coupled to the N-terminal of the peptide-peptoid residue (Gly-Pro-Nleu)$_9$—NH$_2$ in solution. Examples of the preparation of template-linked collagen-like polypeptides are presented in Examples 9–11.

It is important to note that, in the two synthetic routes described above, the amount of the template used is crucial. To exclude the formation of by-products such as compounds with only one chain and/or two chains attached to the template, the equivalents of the template used must be controlled. In a preferred synthesis, the template was added portionwise. In between the additions, the Kaiser test was used to monitor the reaction. In this way, the coupling of the template to the polypeptide-peptoid residue chains normally took 2–3 days, and the functional group equivalents of the template used were generally below 0.9.

The synthetic outline for the template-assembled polypeptide chains are provided in synthesis Schemes 6–8.

V. Conformational Analysis

Biophysical studies on collagen analogs containing peptoid residues according to the invention using spectropolarimetry (CD), ultraviolet spectroscopy (UV), optical rotation measurements (OR) and nuclear magnetic resonance (NMR) show that, when a critical chain length is reached, the peptoid residue-containing sequences of the invention can form a triple helical array.

Collagen-like and polyproline II-like structures exhibit unique CD spectra in solutions (Sakakibara, S. et al. (1968)). These spectra are characterized by a large negative peak around 200 nm and a small positive peak around 217–227 nm. These features have been used as a basis to establish the presence of a polyproline II-like or collagen-like triple helical structure in solution for natural and synthetic peptides (Inouye, K. et al. (1982)). However, these CD spectral shapes and peak positions do not show whether polyproline II-like peptide chains have associated to triple helical structures. Therefore, they cannot be used conclusively, although these parameters are necessary, to establish the presence of a collagen-like triple helical conformation.

The Rpn Index for Helicity

A criterion for evaluating the occurrence and extent of triple helicity in peptide/peptoid residue containing molecules, is provided by the peak intensities and the wavelength of the minimum and maxima of the CD spectra of these molecules. The intensities of both the positive and negative peaks increase as the chain length increases and decrease when the temperature increases. Because the peak intensities and their position depend on many factors, they cannot be used unambiguously to distinguish triple helicity from other structural arrays such as a polyproline II type structure. We have found, however, that an important parameter related to the peak intensities can be useful in establishing the presence of a triple helical array in solution. This parameter is the ratio of the intensities of the positive to negative peak. This parameter is termed Rpn. Unlike the absolute peak intensities, this intensity ratio is more sensitive to conformation. The Rpn is dependent on several factors, such as the solvent, sequence composition, chain length and temperature. However, we have found that within a related series of molecules, Rpn values plotted versus chain length demonstrates an inflection at the critical chain length necessary for triple helix formation.

Melting Curves

Figure 4:
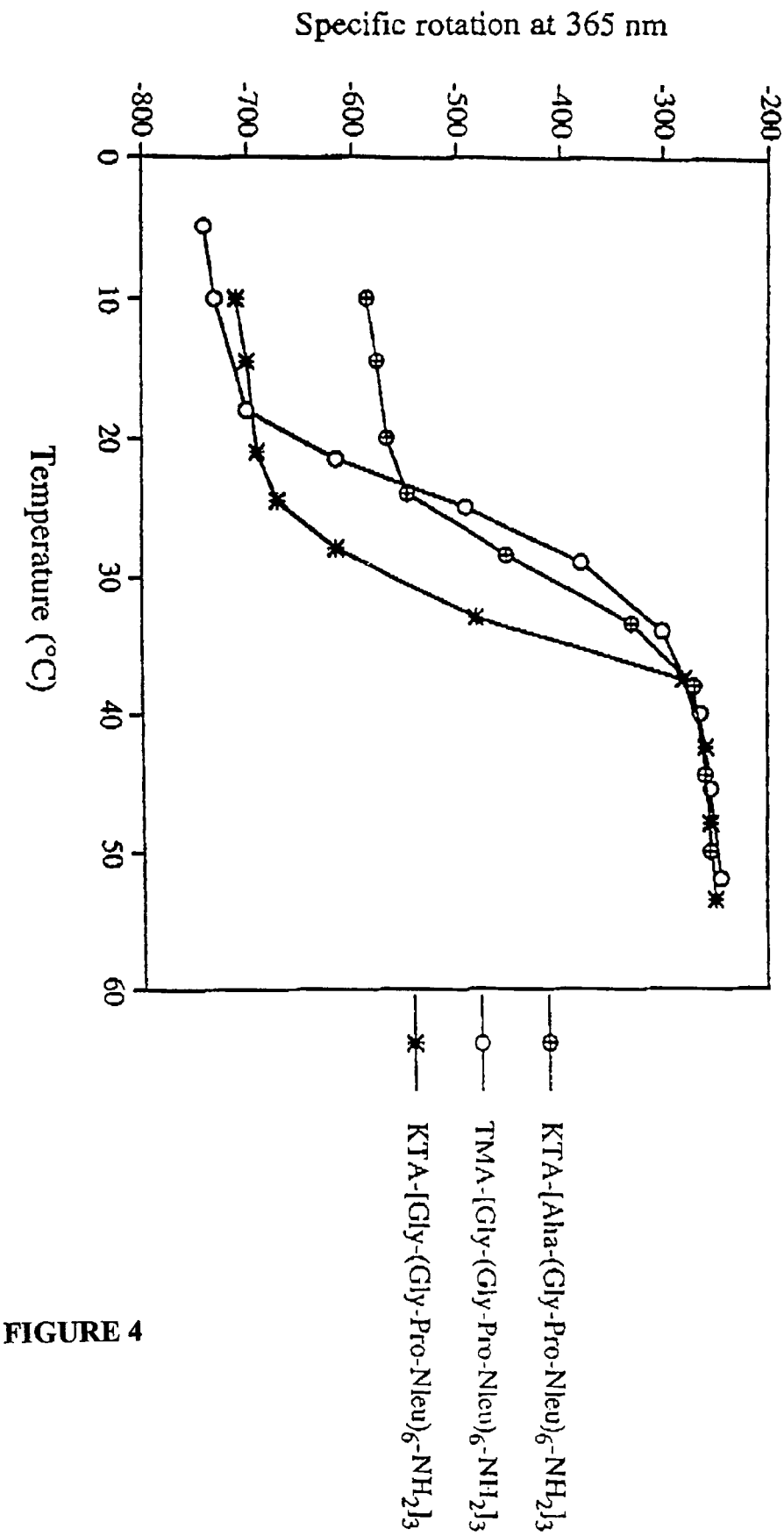
FIG. 4 shows a comparison of melting curves of template bound chains of repeating trimers containing peptoid residues: KTA-[Aha-(Gly-Pro-Nleu)$_6$—NH$_2$]$_3$; TMA-[Gly-(Gly-Pro-Nleu)$_6$—NH$_2$]$_3$; KTA-[Gly-(Gly-Pro-Nleu)$_6$—NH$_2$]$_3$.

Thermal melting measurements describe the change in a physical property of a collagen-like helix, for example the change of specific rotation or UV absorption with temperature. This provides another indication of triple helix formation and stability. Helix formation is indicated by a transition in the rate of change of property with temperature, indicated by an inflection in the melting curve. The transition temperature indicates that temperature above which the helix is denatured. Melting curves for template-bound chains of Gly-Pro-Nleu chains are shown in FIG. 4.

The comparison of biophysical properties between peptoid residue-containing sequences Ac-(Gly-Pro-Nleu)$_9$—NH$_2$ and polypeptide sequences Ac-(Gly-Pro-Pro)$_{10}$ shows that the Gly-Pro-Nleu sequences are comparable to the Gly-Pro-Pro sequences in triple helix thermal stability, although the peptoid residue-containing sequence possesses one trimer repeat less than the peptide compound. This result clearly demonstrates that, contrary to other proline analogs and unnatural imino acid residues, the peptoid residue Nleu is compatible with the collagen triple helical structures. This finding is the first demonstration of new family of collagen-like molecules of the present invention.

In addition, a template can significantly facilitate triple helix formation by allowing a shorter chain to form a triple helical structure and stabilize the triple helical conformations. The system KTA-[Gly-(Gly-Pro-Hyp)$_3$—NH$_2$]$_3$, forms a triple helix, and represents the shortest chain collagen-like triple helix yet reported. Results show that both [KTA-[Gly-(Gly-Pro-Hyp)$_5$—NH$_2$]$_3$ and [KTA-[Gly-(Gly-Pro-Hyp)$_6$—NH$_2$]$_3$ form triple helical structures which can be denatured only above 70° C. in water. The acetyl sequential polypeptides, Ac-(Gly-Pro-Hyp)$_n$—NH$_2$ (n=6,9) can form a stable triple helical structure in water above room temperature although when n=5, a triple helical structure only occurs at <18° C. The effect of the template-spacer is even more dramatic for short chains made up of the Gly-Pro-Hyp trimer. [KTA-[Gly-(Gly-Pro-Hyp)$_3$—NH$_3$]$_3$ is triple helical in water at room temperature, while Ac-(Gly-Pro-Hyp)$_3$—NH$_2$ does not adopt a triple helical structure even in a more favorable solvent system, ethylene glycol:water (v/v 2:1), and at lower temperatures.

This invention similarly includes use of the other peptide-peptoid residue building blocks to form novel collagen-like structures. Of course, co(peptide-peptoid residue) sequences can be included by specific placements of specific building blocks in the collagen-like structures. The sequences of the invention can be analogous to native collagen, comprising either homotrimeric or heterotrimeric chains. Heterotrimeric chains can comprise mixtures of tripeptides and dipeptide-peptoid residue trimers having, for example, the following structure:

(Gly-Hyp-Pro)$_j$ (Gly-Pro-Y$_p$)$_k$ (Gly-Pro-Pro)$_l$ (Gly-Pro-Hyp)$_m$ wherein j,k,l, and m designate the number of repeats for that trimer and the sum of j to m is n, the number of repeating trimeric units. Preferably, there are at least three trimers in the chain (n≧3). The trimers can occur in any order.

The triple helices of the invention can similarly comprise chains of the same sequence of trimers or a different sequence. In any particular case, triple helix formation can be demonstrated as in the Examples.

VI. Experimental Section

Materials: All chiral amino acids used were of L-configuration. Protected amino acids, EDC, DCC and benzotriazolyloxytris(dmethylamino)phosphoniumhexafluoropho sphate (BOP) were purchased from Bachem. ACS-grade and HPLC-grade solvents (DCM, DMF, H2O acetonitrile, chloroform, methanol, ethyl acetate, hexane, THF) were purchased from Fisher Scientific and used without further purification. TEA, Pd/C, and p-nitrophenol were purchased from Aldrich. HOBt, TFA(HPLC grade) and HCl/dioxane(4N) were purchased from Chem-Impex International.

General Information: All reactions in solution were monitored by thin-layer chromatography (TLC) carried out on precoated silica gel 60F-54 plates (Merck) using solvent systems chloroform/methanol/acetic acid (CMA) or ethyl acetate/hexane (E/H). Compounds were visualized by UV, ninhydrin or bromocresol solutions. Silica gel 60 (Merck, 0.040–0.063 mm, 230–400 mesh ASTM) was used to run column chromatography. Two types of HPLC instruments were used to analyze and purify the products. One is a Waters (510 pump, 484 detector) system. Another is the MILLENNIUM 2010 system consisted of a Waters 715 Ultra WISP sample processor, a Waters TM 996 photodiode array detector, two Waters 510 pumps and a NEC PowerMate 486/33I computer. Solvents used in HPLC were solvent A: H2O with or without 0.1% TFA, solvent B: acetonitrile with or without 0.1% TFA. The flow rate was 10 ml/min. for preparatory column, 4 ml/min. for semipreparatory column, and 1.0–1.2 ml/min. for analytical column.

NMR: The NMR spectra were used to verify the structures of the intermediates and small peptides. For some compounds, 2-D NMR (COSY and HOHAHA) spectra were measured to determine peak assignments. These spectra were obtained on either a Bruker AMX 500 MHz Spectrometer or using an 360 MHz spectrometer assembled in house with a Techmag pulse programmer and digitizer, and an Oxford Instruments Superconducting magnet.

Circular dichroism (CD): Measurements were carried out on a modified Cary-61 Spectropolarimeter. CD spectra were obtained with a 0.02 cm cell, by signal-averaging 10 scans. The wavelength range was set between 185–300 nm, the scan speed was 1.0 nm per second. The sample was measured at a concentration 0.2 mg/ml. To allow for proper equilibration of triple helix formation, the solution was kept in a refrigerator (~4° C.) for at least 24 hours prior to each experiment and another 2 hours at the specified temperature before acquiring data.

UV: The ultraviolet (UV) melting curve was carried out on a Cary-1E UV Spectrometer. The sample concentration was 0.04 mg/ml and was prepared from the 0.2 mg/ml solution for the CD measurements. The solution was kept in a refrigerator (4° C.) at least 24 hours before experiment. To perform the melting experiments, the sample was equilibrated one hour at the starting temperature. The heating rate was 0.2 degree per minute. The measuring wavelength was set at 223 nm.

MS: Mass spectra were obtained at UC Riverside and the Scripps Research Institute. Fast atom bombardment (FAB), electrospray ionization (ESI) and matrix-assisted laser desorption ionization (MALDI) methods were used to verify the structures of the products.

SYNTHESIS SCHEMES 1–8

Scheme 1
Method 1:
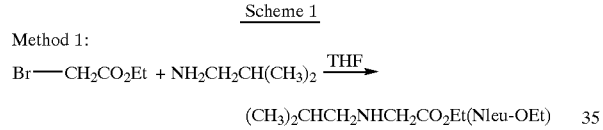

Method 2:
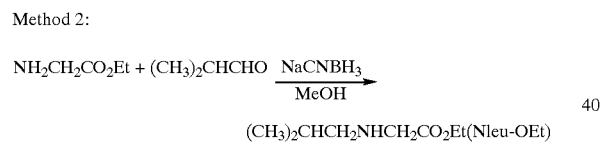

Scheme 2
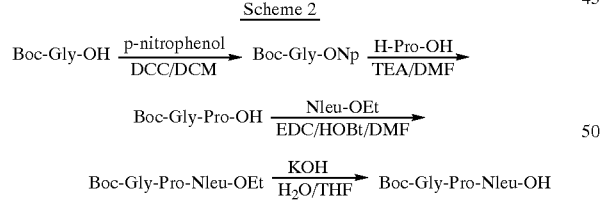

Scheme 3
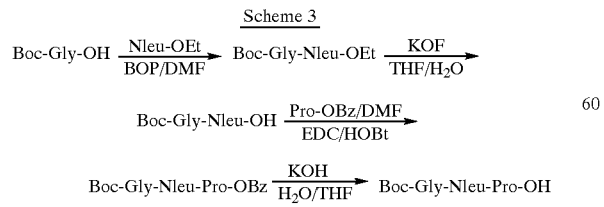

Scheme 4
MBHA Resin
| 1, TEA/DCM, 10%
| 2, Boc-Xaa-Yaa-OH (1.2–1.5 equiv.)
|    Diisopropylcarbodiimide (DIC), HOBt
|    DCM + DMF (25%), 2–4 hours Boc-Gly-Xaa-Yaa-Resin
[ 1, TFA/DCM, 33%
  2, TEA/DCM, 10%
  3, Boc-Xaa-Yaa-OH (1.2–1.5 equiv.)   ] X(n-1)
     DIC, HOBt, DCM + DMF (25%),
     4–8 hours Boc-(Gly-Xaa-Yaa)$_n$-Resin 1, TFA/DCM, 33%          1, TFA/DCM, 33%
2, HF cleavage            2, TEA/DCM, 10%
3, RP HPLC                3, Acetic anhydride,
                             DCM, TEA, 1 hour
                          4, HF cleavage
                          5, RP HPLC (Gly-Xaa-Yaa)$_n$-NH$_2$    Ac-(Gly-Xaa-Yaa)$_n$-NH$_2$ Scheme 5
Synthesis of Ac-Gly-Pro-Nleu-NH$_2$ in solution Boc-Gly-Pro-Nleu-OH $\xrightarrow[\text{EDC/HOBt}]{\text{NH}_4\text{Cl/TEA/DMF}}$ Boc-Gly-Pro-Nleu-NH$_2$ $\xrightarrow[\text{2, HCl/dioxane}]{\text{1, TFA/DCM}}$ HCl·Gly-Pro-Nleu-NH$_2$ $\xrightarrow[\text{TEA/DCM}]{\text{Acetic anhydride}}$ Ac-Gly-Pro-Nleu-NH$_2$ Scheme 6
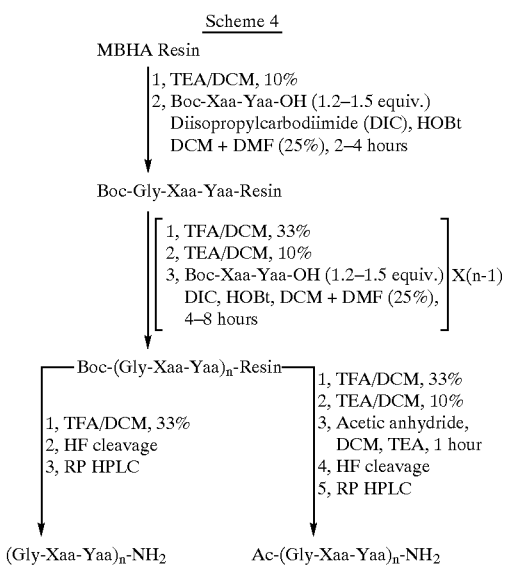
Kemp triacid (KTA)

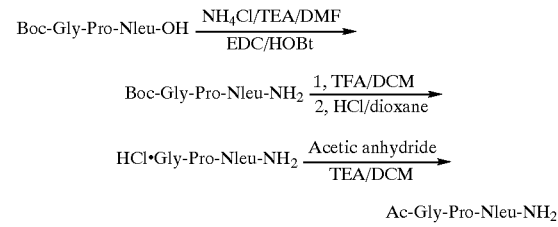
KTA-(Aha-OBz)$_3$

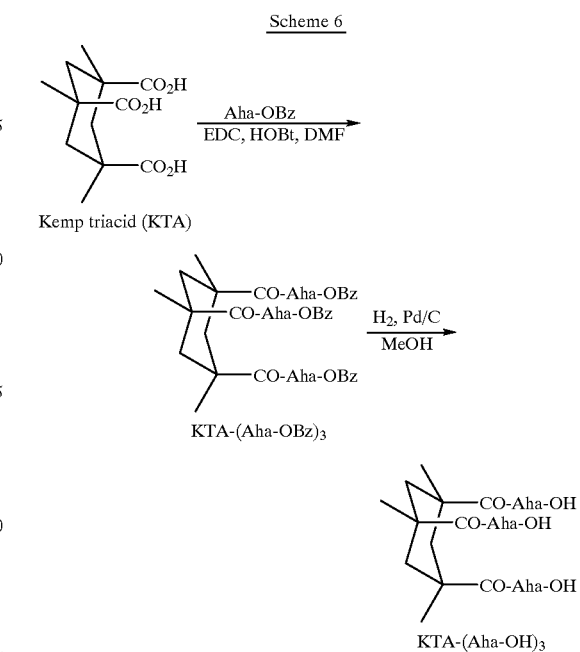
KTA-(Aha-OH)$_3$

-continued

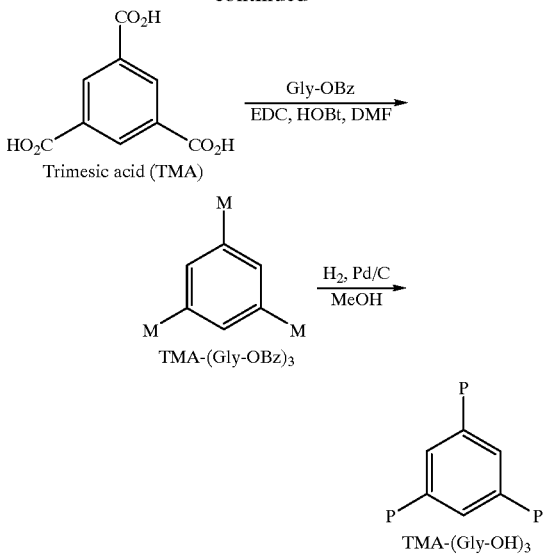

Aha: NH₂———(CH₂)₅———CO

M = CO-Gly-OBz

P = CO-Gly-OH

Scheme 7
Solidphase method:
Boc-(Gly-Xaa-Yaa)$_n$-MBHA

| 1, TFA/DCM, 30%
| 2, TEA/DCM, 10%
| 3, templates, 0.3 equiv.
|    DIC/HOBt, 3 days
|    DMF/DCM
↓

Template-[(Gly-Xaa-Yaa)$_n$]$_3$-MBHA

| 1, HF cleavage
| 2, RP-HPLC separation
↓

Template-[(Gly-Xaa-Yaa)$_n$-NH₂]$_3$

Scheme 8
Solution method
(Gly-Pro-Nleu)$_n$-NH₂ + Template

| 1, EDC/HOBt/DMF
|    3 days
| 2, Dialysis in water
| 3, HPLC separation
↓

Template-[Gly-(Gly-Pro-Nleu)$_n$-NH₂]$_3$

EXAMPLE 1

Synthesis of the Trimer Building Block Boc-Gly-Pro-Hyp(OBz)—OH

Boc-Gly-Pro-OBz

Boc-Gly-OH (35 g, 0.2 mol.), Tos-Pro-OBz (75.5 g, 0.2 mol.) and HOBt (30 g, 0.22 mol.) were dissolved in 600 ml DMF. The solution was cooled on an ice water bath and TEA (35 ml, 0.25 mol.) was added slowly. After 5 minutes, EDC (40 g, 0.21 mol.) was added. After stirring the solution at 0° C. for one hour, the bath was removed and the solution was stirred at room temperature overnight. The DMF was removed under reduced pressure. The remaining mixture was decanted into 800 ml ethyl acetate. The ethyl acetate solution was washed with 2×200 ml H₂O 3×100 ml saturated NaHCO₃, 2×100 ml saturated NaCl (brine), 3×100 ml 2N NaHSO₄ and brine until the pH of the brine layer was approximately 7. The solution was dried using Na₂SO₄ and the solvent was removed to obtain the crude product. Column chromatography (elution solvent: ethyl acetate/hexane 2:1) was carried out to give the pure compound (white solid, 69 g, 95.5%). TLC Rf=0.42 (ethyl acetate/hexane, 3:1).

Boc-Gly-Pro-OH

The Boc-Gly-Pro-OBz (19.4 g, 0.054 mol.) was dissolved in a mixture of 100 ml H₂O and 100 ml THF. After cooling the solution to 0° C., KOH (4.8 g, 0.085 mol.) in 50 ml H₂O was added slowly. The solution was stirred for one hour. Then, the THF was removed under reduced pressure and the aqueous solution was extracted with ethyl acetate to remove the benzyl alcohol. The resulting aqueous phase was covered by 200 ml ethyl acetate and was acidified at 0° C. to about pH 2 by addition of concentrated HCl slowly (vigorously swirling the solution at the same time). The product was extracted from the aqueous phase with ethyl acetate 3×200 ml. The organic layers were combined and washed with brine 2×30 ml, and dried by Na₂SO₄. Removal of the ethyl acetate gave the product Boc-Gly-Pro-OH (white solid, 12.3 g, 85%) TLC Rf=0.25 (CMA, 85:15:3) FAB-MS, observed MH⁺=273. ¹H-NMR (360 MHz, DMSO-d₆, 20° C.) δ 12.55 (s, 1H, carboxyl), 6.79 (s, NH-major), 4.50 (dd, 0.25H, Pro α-minor), 4.20 (dd, 0.71H, Pro-α-major), 3.81–3.62 (m, 1.7H, Gly-α-major) 3.47–3.33 (m, 2H, Pro-δ and Gly-α-minor), 2.25–2.00 (m, 1.2H, Pro-β), 1.96–1.60 (m, 2.7H, Pro-β and Pro-γ), 1.36 (s, 9H, Boc).

Synthesis of Boc-Gly-Pro-ONp

Boc-Gly-Pro-OH (2.8 g, 0.01 mol.) and p-nitrophenol (1.7 g, 0.012 mol.) were dissolved in DCM (100 ml) and DCC (2.1 g, 0.01 mol.) was added to the solution by portions while stirring the solution. A precipitate (dicyclohexylurea, DCU) soon formed. After stirring the solution at room temperature for 3.5 hours, TLC analysis (developing solvents:ethyl acetate/hexane, 3:1) showed that all the starting material Boc-Gly-Pro-OH was consumed. The Rf for the product Boc-Gly-Pro-ONp is 0.45 in this solvent system. DCU was removed by filtration and DCM was removed under reduced pressure. Ethyl acetate was added to the remaining oil and the resulting solution was chilled to 0° C. More precipitate formed and was removed by filtration. The above procedures were repeated and a brownish oil was obtained. The product was directly used in the synthesis of Boc-Gly-Pro-Hyp(OBz)—OH without further purification and characterization.

Boc-Hyp(OBz)—OH

Portions of Boc-Hyp-OH (9.3 g, 0.04 mol.) were added to about 200 ml liquid ammonia, the reaction flask was placed on a dry ice-isopropanol bath. The solution was stirred for 5 minutes. Sodium (1.8 g, 0.08 mol.) was added, the solution became dark blue. After 5 minutes, benzyl chloride (8 ml, 0.069 mol.) was added slowly, and the blue color disappeared. The reaction solution was stirred at −79° C. for 2 hours, and the bath was removed with continuous stirring until the ammonia was almost gone (another 3 hours). To the resulting reaction mixture, 150 ml H₂O was added carefully. The aqueous solution was extracted with ethyl acetate 2×100 ml to remove unreacted benzyl chloride. Then, the aqueous solution was covered by 200 ml ethyl acetate and was acidified at 0° C. to pH 3 by addition of concentrated HCl slowly (vigorously swirling the solution at the same time). The products were extracted from the aqueous solution with ethyl acetate 2×200 ml. Two compounds were found in the organic layer by TLC analysis (developing solvents: chloroform/methanol/acetic acid (CMA), 85:15:3). They were verified by NMR to be the expected product Boc-Hyp(OBz)—OH (Rf, 0.36). The ethyl acetate solution was dried by $Na_2SO_4$ and the solvent was removed under reduced pressure. Column chromatography (elution solvents: ethyl acetate/hexane, 3:1) was used to separate the mixture. 3.7 g Boc-Hyp-OH was recovered and 7.5 g product Boc-Hyp(OBz)—OH (white solid, 58.4%) was obtained. FAB-MS, observed $(M+H)^+=322$. $^1$H-NMR (360 MHz, DMSO-$d_6$, 20° C.) δ12.48 (s, 1H, $CO_2H$), 7.31 (m, 5H, phenyl), 4.48 (q, 2H, benzyl), 4.11 (m, 2H, 1H for Hyp-α and 1H for Hyp-γ), 3.43 (m, 1H, Hyp-δ-1), 3.25 (m, 1H, Hyp-δ-h), 2.34 (m, 1H, Hyp-β-1), 1.98 (m, 1H, Hyp-β-h), 1.36 (d, 9H, Boc) Boc-Gly-Pro-Hyp(OBz)—OH Boc-Hyp(OBz)—OH (3.2 g, 0.01 mol.) and 50 ml TFA/DCM (30%) were mixed and the solution was stirred at room temperature for a half hour. TLC analysis showed the absence of Boc-Hyp(OBz)—OH (Rf=0.52 in CMA 85:15:3). The solvents were removed and toluene was added (3×50 ml) and distilled to remove trace TFA. The TFA salt of Hyp(OBz)—OH obtained above was dissolved in DMF. The solution was stirred and chilled to 0° C. on a water-ice bath. Triethylamine was added to the solution slowly until the pH was about 9. Then, Boc-Gly-Pro-ONp (0.01 ml) was added and the resulting solution was stirred for one hour. The bath was removed and the stirring was continued overnight. The solvents were distilled under reduced pressure and the remaining mixture was poured into 50 ml saturated $NaHCO_3$. The aqueous solution was extracted with ethyl acetate 2×50 ml to remove organic impurity. The remaining aqueous solution was covered by 100 ml ethyl acetate and was acidified at 0° C. to about pH 2 by addition of concentrated HCl slowly (swirling the solution vigorously at the same time). The product was extracted from the aqueous solution with ethyl acetate 2×150 ml. The organic layers were combined and washed with brine 2×15 ml and dried by $Na_2SO_4$. The solvent was removed under reduced pressure to obtain the crude product. Column chromatography (elution solvent: ethyl acetate/hexane 3:1) was carried out to obtain the pure product (white solid, 2.6 g, 55%). TLC, Rf=0.42 (CMA, 85:15:3). Analytical RP-HPLC chromatogram showed a single homogeneous peak with retention time RT=13.8 minute (0.1% TFA in the elution solvents, 30–60% B, 25 minutes). FAB-MS, observed $(M+H)^+=476$. 1H-NMR (500 MHz, DMSO-$d_6$, 27° C., assignment by HOHAHA. (l and h represent low and high fields) δ 12.36 (s, 1H, $CO_2H$), 7.34 (m, 5H, phenyl), 6.74 (d, 1H, NH), 4.92 (dd, 0.3H, Pro-α, minor), 4.63 (dd, 0.7H, Pro-α, major), 4.52 (q, 2H, benzyl), 4.32–4.20 (m, 2H, Hyp-α and Hyp-γ), 4.21 (d, 0.35H, Hyp-δ-minor-1), 3.92 (d, 0.65H, Hyp-δ-major-1), 3.80 (m, 1H, Gly-α-1), 3.70–3.60 (m, 1.65H, 1H for Gly-α-h, 0.65H for Hyp-δ-major-h), 3.54 (d, 0.35H, Hyp-δ-minor-h), 3.47–3.36 (m, 2H, Pro-δ), 2.40–2.20 (m, 1.5H, Hyp-β-1 and Pro-β-1-minor), 2.10–1.84 (m, 3.2H, Pro-β-1-major, Pro-β-h-minor, Hyp-β-h-minor, Hyp-β-h-major and Pro-δ-major), 1.80–1.60 (m, 1.3H, Pro-β-h-major, Pro-γ-1-minor and Pro-γ-h-minor), 1.36 (s, 9H, Boc).

EXAMPLE 2

Synthesis of Collagen Analogs Composed of Gly-Pro-Hyp Trimers

Ac-Gly-Pro-Hyp-$NH_2$

Boc-Gly-Pro-Hyp-(OBz)-MBHA (0.3 mmol. based on the resin substitution) was prepared following the general solid phase segment condensation procedure described in the section on General Information. The Boc protecting group was removed using a solution of 15 ml 30% TFA in DCM, 1.0 ml anisol was added as scavenger. The resin was washed with 20 ml DCM, 20 ml methanol, 20 ml DCM and followed by 2×15 ml 10% TEA in DCM. the n-termini were acetylated using 0.5 ml acetic anhydride dissolved in 15 ml DCM with 5% TEA to give Ac-Gly-Pro-Hyp(OBz)-MBHA. After carrying out the HF cleavage (General Information section), 72 mg crude material was obtained. RP-HPLC was carried out to obtain the pure product Ac-Gly-Pro-Hyp-$NH_2$ (white solid, 45 mg, 46%). The analytical HPLC gave a homogeneous single peak chromatogram. FAB-MS, observed $(M+H)^+=327.1678$, calculated $(M+H)^+=327.1668$. $^1$H-NMR (500 MHz, $D_2O$, using $H_2O$ for obtaining NH signals, 27° C. Assignment by DQF-COSY method) δ 8.14 (s, 1H, Gly-NH), 7.75 (s, 1H, C-terminal $NH_2$), 7.01(s, 1H, C-terminal $NH_2$), 4.95 (dd, 0.15H, Pro-α), 4.74 (m, covered in $H_2O$ signal, Pro-α), 4.62 (m, 1H, Hyp-γ) 4.53 (t, 1H, Hyp-α), 4.15 (d, 1H, Gly-α-a), 4.00 (d, 1H, Gly-α-h), 3.88 (d, 1H, Hyp-δ-1), 3.81 (dd, 1H, Hyp-δ-h), 3.60 (m, 2H, Pro-δ), 2.34 (m, 2.1H, Hyp-β-l), Pro-β-l), 2.06 (m, 5.6H, Hyp-β-h, Pro-γ and acetyl), 1.93 (m, 1.3H, Pro-β-l). Ac-(Gly-Pro-Hyp)$_n$—$NH_2$(n=3,5,6,9).

The synthesis, purification and characterization of these compounds were similar to that of Ac-Gly-Pro-Hyp-$NH_2$. The results of the synthesis of the Gly-Pro-Hyp compounds are summarized in Table 1.

EXAMPLE 3

Synthesis of the KTA Template-Assembled Collagen-like Structures: (Gly-Pro-Hyp)$_n$ KTA-[Gly-Gly-Pro-Hyp-$NH_2$]$_3$ Boc-Gly-Pro-Hyp(OBz)-MBHA (0.3 mmol based on resin substitution level) was prepared following the general solid phase synthesis procedure described in the section on General Information. The Boc group was removed using a solution of 30% TFA in DCM and 1.0 ml anisol was added as scavenger. The resin was washed with DCM, methanol, 10% TEA in DCM and DCM to give Gly-Pro-Hyp(OBz)-M3HA. KTA-(Gly-OH)$_3$ (35 mg, 0.08 mmol) and HOBt (50 mg) were added to the vessel and about 25% DMF was added to help dissolve the HOBt. Then, 4 ml 1.0 M DIC (0.4 mmol) in DCM was added. The Kaiser test showed the absence of free amines after shaking the vessel for 3 days. The resin was washed by DCM and methanol several times and dried in a desiccator overnight. The HF cleavage methods (described in the General Information section) were carried out to remove the peptide from the resin, and the resulting mixture of resin and product was washed with a hexane and ethyl ether mixture. The product was separated from the resin by extracting with $H_2O$. The extracted $H_2O$ solution was lyophilized to obtain the crude product. RP-HPLC was carried out to give the pure product (white solid, 55 mg, 56% yield). The analytical HPLC profile showed a single homogeneous peak with RT=13 minute (no TFA, 7–50% B, 30 minutes). ESI-MS, M+Na)$^+$=1251. $^1$H-NMR (500 MHz, $D_2O$, 27° C., using $H_2O$ at 5° C. to obtain NH signals, DQF-COSY)δ 8.84 (m, 3H, Gly-NH), 8.57 (m, 3H, spacer Gly-NH), 7.89 (m, 3H, terminal $NH_2$), 7.33 (m, 3H, terminal $NH_2$), 4.61(m, 3H, Hyp-γ), 4.49 (t, 3H, Hyp-α), 4.06 (q, 6H, Gly-α), 3.86–3.70 (m, 12H, spacer Gly-α and Hyp-δ), 3.67–3.54 (m, 6H, Pro-δ), 2.65 (d, 3H, methylene equatorial), 2.37–2.26 (m, 6H, Pro-β and Hyp-β), 2.10–2.00 (m, 9H, Pro-γ and Hyp-β), 1.97–1.90 (m, 3H, Pro-β), 1.33 (d, 3H, methylene-axial), 1.26 (s, 9H, methyl). KTA-[Gly-(Gly-Pro-Hyp)$_n$—$NH_2$]$_3$ (n=3,5,6)

The synthesis and characterization procedures for these three compounds were similar to that of KTA-[Gly-(Gly-Pro-Hyp-NH$_2$]$_3$. The results are shown on Table 1 below.

TABLE 1

Physicochemical Data for the Synthesized Compounds

| Compounds | MW | MS results | HPLC RT (min)[a] | Yields[b] |
|---|---|---|---|---|
| Ac—Gly—Pro—Hyp—NH$_2$ | 326 | FAB MH$^+$, 327 | 5.7 3–30% B, 25 min.[c] | 46% |
| Ac—(Gly—Pro—Hyp)$_3$—NH$_2$ | 861 | ESI MNa$^+$, 883 | 14.1 4–40% B, 30 min. | 42% |
| Ac—(Gly—Pro—Hyp)$_5$—NH$_2$ | 1396 | FAB MNa$^+$, 1418 | 16.5 4–40% B, 30 min | 35% |
| Ac—(Gly—Pro—Hyp)$_6$—NH$_2$ | 1663 | ESI MNa$^+$, 1685 | 17.3 4–40% B, 30 min. | 39% |
| KTA—[Gly—Gly—Pro—Hyp—NH$_2$]$_3$ | 1228 | ESI MNa$^+$, 1251 | 13 7–50% B, 30 min.[c] | 56% |
| KTA—[Gly—(Gly—Pro—Hyp)$_3$—NH$_2$]$_3$ | 2832 | ESI MNa$^+$, 2854 | 19.9 4–40% B, 30 min. | 35% |
| KTA—[Gly—(Gly—Pro—Hyp)$_5$—NH$_2$]$_3$ | 4436 | MALDI MNa$^+$, 4457 | 18.9 4–40% B, 30 min. | 12% |
| KTA—[Gly—(Gly—Pro—Hyp)$_6$—NH$_2$]$_3$ | 5238 | MALDI MNa$^+$, 5261 | 18.8 4–40% B, 30 min. | 10% |

[a]Vydac analytical column. Elution solvents: A, H$_2$O, 0.1% TFA. B, acetonitrile 0.1% TFA.
[b]The yields were calculated based on the resin substitution level and the materials obtained from RP-HPLC purification.
[c]No TFA in the elution solvents.

EXAMPLE 4

Synthesis of Peptoid Residue Xp as Nleu-OEt

Nleu-OEt by Alkylation

Isobutylamine (50 g, 0.68 mol.) was dissolved in 300 ml THF and the solution was chilled to 0° C. Ethyl bromoacetate (50 g, 0.3 mol.) was added slowly while stirring the solution. The stirring was continued for 3 hours. The THF was removed under reduced pressure and the resulting mixture was poured into 300 ml ethyl acetate. A precipitation of the hydrogen bromide salt of isobutylamine formed and was removed by filtration. The ethyl acetate was distilled under reduced pressure in a rotovapor until about 50 ml solution was left. Column chromatography (elution solvents: E/H, 3:1) was performed to purify the product. TLC RF=0.5 (developing solvents, E/H, 3:1). The collected eluent from the chromatography was combined and chilled to 0° C. HCl in dioxane (4N) was added until no more precipitation was observed. The product was precipitated out in the form of a hydrogen chloride salt (white solid, 49 g, 83%).

Nleu-OEt by Reductive Amination

The hydrogen chloride salt of Gly-OEt (14 g, 0.1 mol.), isobutylaldehyde (7.3 g, 0.1 mol.) and KOH (1 g) were dissolved in 200 ml methanol. The solution was chilled to 0° C. on a water-ice bath and was stirred for one hour. NaCNBH$_3$ (5.7 g, 0.09 mol.) was added slowly. The stirring was continued overnight. The methanol was removed under reduced pressure and the resulting mixture was poured into 300 ml ethyl acetate. The product was extracted out from the organic phase by saturated NaHSO$_4$ 5×50 ml. The aqueous phase was chilled to 0° C. and the pH was adjusted to about 9 by addition of NaHCO$_3$ slowly while swirling the solution vigorously. The free amine form of the product was extracted out from the aqueous solution by ethyl acetate 3×100 ml. The organic phase was dried by Na$_2$SO$_4$ and the ethyl acetate was removed under reduced pressure to obtain the crude product. Column chromatography (elution solvents: E/H, 4:1) was carried out to obtain the pure product (oil, 11.5g, 72%). TLC Rf=0.55 (developing solvents: chloroform/methanol, 4:1). FAB-MS, observed (M+H)$^+$= 160. $^1$H-NMR (360 MHz, DMSO-d6, 20° C.) for the HCl salt, δ 9.16 (s, 2H, NH$_{2+}$), 4.20 (q, 2H, OCH$_2$), 3.91 (s, 2H, α CH$_2$), 2.74 (d, 2H, isobutyl CH$_2$), 1.94 (m, 1H, isobutyl CH), 1.20 (t, 3H, ethyl CH$_3$), 0.90 (d, 6H, isobutyl CH$_3$).

EXAMPLE 5

Synthesis of Trimer Building Block Boc-Gly-Pro-Nleu-OH

Boc-Gly-ONp

Boc-Gly-OH (32.6 g, 0.186 mol.) and p-nitrophenol (27.8 g, 0.20 mol.) were dissolved in 300 ml dichloromethane (DCM) and the solution was chilled to 0° C. on a water-ice bath. Dicyclohexylcarbodiimide (DCC, 39 g, 0.19 mol.) was added by four portions while stirring the solution. A precipitation of dicyclohexylurea (DCU) shortly formed. The solution was stirred at room temperature overnight and TLC analysis showed no more starting material Boc-Gly-OH. The DCU was removed by filtration. The resulting solution was chilled to 4° C., more precipitation formed and was removed by filtration. The DCM was removed under reduced pressure to obtain a yellow oil. The oil was put on a vacuum system overnight and ether/hexane was used to scratch out the product Boc-Gly-ONp (white solid, 50 g, 91%). TLC Rf=0.7 (developing solvents: CMA, 85:15:3).

Boc-Gly-Pro-OH

Boc-Gly-ONp (50 g, 0.17 mol.) and proline (20.7 g, 0.175 mol.) were dissolved in 300 ml DMF. 20 ml TEA and 30 ml water were added while stirring the solution. The stirring was continued overnight and TLC analysis showed no more starting materials. The solvents were removed under reduced pressure and the resulting mixture was dissolved in 250 ml saturated Na$_2$CO$_3$. The aqueous solution was extracted by 3×100 ml ethyl acetate to remove p-nitrophenol. Then, after chilling to 0° C., the aqueous solution was acidified to about pH=3 by addition of concentrated HCl slowly (vigorously swirling the solution at the same time). The product was extracted from the aqueous phase by 3×150 ml ethyl acetate. The organic phase was combined and washed by saturated NaCl (brine) 3×20 ml, and dried using Na$_2$SO$_4$. TLC analysis showed there was still p-nitrophenol in the solution. The ethyl acetate was removed under reduced pressure and column chromatography (elution solvents: E/H, 2:1) was carried out to obtain the pure product Boc-Gly-Pro-OH (white solid, 41.2 g, 88%). TLC Rf=0.25 (CMA, 85:15:3). FAB-MS, observed $(M+H)^+$=273. $^1$H-NMR (360 MHz, DMSO-d6, 20° C.) δ 12.55 (s, 1H, carboxyl), 6.79 (s, NH-major), 6.44 (s, NH-minor), 4.50 (dd, 0.25H, Pro-α-minor), 4.20 (dd, 0.71H, Pro-α-major), 3.81–3.62 (m, 1.7H, Gly-α-major), 3.47–3.33 (m, 2.5H, Pro-δ and Gly-α-minor), 2.25–2.00 (m, 1.2H, Pro-β), 1.96–1.60 (m, 2.7H, Pro-β and Pro-γ), 1.36 (s, 9H, Boc-CH$_3$)b.

Boc-Gly-Pro-Nleu-OEt

Boc-Gly-Pro-OH (3.85 g, 0.014 mol), the HCl salt of Nleu-OEt (2.76 g, 0.014 mol) and HOBt (2.8 g, 0.02 mol.) were dissolved in 100 ml DMF and the solution was chilled to 0° C. on a water-ice bath. TEA (2.8 ml, 0.02 mol.) was added to the solution. After stirring the solution for 10 minutes, EDC (4.0 g, 0.021 mol.) was added. The stirring was continued overnight. The DMF was removed under reduced pressure and the resulting mixture was poured into 200 ml ethyl acetate. The organic layer was washed by H$_2$O 2×30 ml, saturated NaHCO$_3$ 3×10 ml, brine 2×10 ml, saturated NaHSO$_4$ 3×15 ml and brine again until the pH value of the brine layer was approximately 7. The ethyl acetate solution was dried using Na$_2$SO$_4$ and the solvent was removed by distillation under reduced pressure. Column chromatography (elution solvents: E/H, 2:1) was performed to obtain the pure product (yellowish oil, 4.7 g, 81%). TLC Rf=0.54 (developing solvents: CMA, 85:15:3) and Rf=0.34 (developing solvents: E/H, 2:1).

Boc-Gly-Pro-Nleu-OH

Boc-Gly-Pro-Nleu-OEt (4.3 g, 0.0104 mol.) was dissolved in 80 ml THF/H$_2$O (v/v, 1:1) and the solution was chilled to 0° C. on a water-ice bath. KOH (1.1 g dissolved in 20 ml H$_2$O) was added while stirring the solution. After a while, the bath was removed and the stirring was continued for one more hour. The THF was removed under reduced pressure. The aqueous solution was extracted by ethyl acetate 2×50 ml. Then, the aqueous layer was chilled to 0° C. and was acidified to about pH=3 by addition of concentrated HCl while swirling the solution vigorously at the same time (the aqueous layer was covered by 50 ml ethyl acetate). The product was extracted from the aqueous layer by ethyl acetate 3×50 ml. The organic layer was combined and dried by Na$_2$SO$_4$. The ethyl acetate was removed under reduced pressure. Column chromatography (E/H:5:2) was carried out to obtain the pure product (white solid, 3.6 g, 92%). TLC Rf=0.44 (developing solvents: CMA, 85:15:3). FAB-MS, observed $(M+H)^+$=386. Analytical RP-HPLC chromatogram, single peak, retention time RT=13 min. (25–60% B in 30 min.). $^1$H-NMR (500 MHz, DMSO-d6, 25° C., assignment by TOCSY) δ 12.50 (s, 1H, carboxyl), 6.62 (m, 1H, Gly-NH), 4.92 (d, Pro-α), 4.72 (d, Pro-α), 4.56 (d, Nleu-α), 4.48 (d, Pro-α), 4.12 (m, Nleu-α), 4.00–3.90 (m, Nleu-α), 3.83–3.66 (m, Nleu-α, Gly-α), 3.64–3.50 (m, Gly-α, Nleu-α), 3.50–3.33 (m, Pro-δ), 2.34–1.60 (sets of bands, Pro-β, Pro-γ, Nleu-γ), 1.38 (s, 9H, Boc-CH$_3$), 0.88 (dd, Nleu-δ), 0.75 (dd, Nleu-δ).

EXAMPLE 6

Synthesis of Trimer Building Block Boc-Gly-Nleu-Pro-OH.

Boc-Gly-Nleu-OEt

Boc-Gly-OH (4.4 g, 0.025 mol.) and Nleu-OEt (3.2 g, 0.02 mol.) were dissolved in 100 ml DMF and the solution was chilled to 0° C. on a water-ice bath. BOP (11 g, 0.025 mol.) was added to the solution. Triethylamine was used to adjust the pH of the solution to about 9. The solution was stirred overnight. The DMF was removed under reduced pressure and the resulting mixture was poured into 300 ml ethyl acetate. The ethyl acetate solution was washed by H$_2$O, saturated NaHCO$_3$, brine, saturated Na$_2$SO$_4$ and brine again. The organic layer was dried by Na$_2$SO$_4$ and the ethyl acetate was removed under reduced pressure to get the crude product. Column chromatography (elution solvents: E/H, 2:1) was carried out to obtain the pure product (5.9 g, 94%). TLC Rf=0.52 (developing solvents: E/H, 2:1). $^1$H-NMR (360 MHz, DMSO-d6) δ 6.74 (m, Gly-NH), 6.68 (m, Gly-NH), 4.18 (s, Nleu-α), 4.12 (q, ethyl ester-CH$_2$), 4.04 (q, ethyl ester-CH$_2$), 3.94 (s, Nleu-α), 3.79 (d, Gly-α), 3.65 (d, Gly-α), 3.07 (m, Nleu-β), 1.79 (m, 1H, Nleu-γ), 1.34 (s, 9H, Boc-CH$_3$), 1.16 (m, ethyl ester-CH$_3$), 0.87 (d, Nleu-δ), 0.78 (d, Nleu-δ).

Boc-Gly-Nleu-OH

Boc-Gly-Nleu-OEt (28.8 g, 0.094 mol.) was dissolved in a mixture of 150 ml H$_2$O and 150 ml THF. KOH (11.9 g, 0.18 mol.) dissolved in 50 ml H$_2$O was added while stirring the solution. After one hour, The THF was removed under reduced pressure. The aqueous solution was chilled to 0° C. and acidified to about pH=2 by addition of concentrated HCl (swirling the solution vigorously at the same time). The product was extracted from the aqueous layer by ethyl acetate 3×100 ml. The organic layers were combined, washed by brine and dried by Na$_2$SO$_4$. The ethyl acetate was removed under reduced pressure to get the crude product. Column chromatography (elution solvents: E/H, 1:1. This solvent system was used to remove the impurities and the pure product was washed out from the column by a mixture of methanol and ethyl acetate) was carried out to obtain the pure product (white oil, 20 g, 74%). TLC Rf=0.2 (developing solvents: E/H, 3:1). FAB-MS, observed $(M+H)^+$=289. $^1$H-NMR (360 MHz, DMSO-d6) d 6.72 (m, Gly-NH), 6.62 (m, Gly-NH), 4.03 (s, Nleu-α), 3.87 (s, Nleu-α), 3.78 (d, Gly-α), 3.68 (d, Gly-α), 3.06 (m, Nleu-β), 1.82 (m, 1H, Nleu-γ), 1.32 (s, 9H, Boc-CH$_3$), 0.85 (d, Nleu-δ), 0.76 (d, Nleu-δ).

Boc-Gly-Nleu-Pro-OBz

Boc-Gly-Nleu-OH (12.5 g, 0.043 mol.), HCl•Pro-OBz (11 g, 0.046 mol.) and HOBt (6.0 g, 0.045 mol.) were dissolved in 300 ml DMF and the solution was chilled to 0° C. Triethylamine (12 ml) was added slowly while stirring the solution. After 5 minutes, EDC (8.5 g, 0.043 mol.) was added to the solution and the stirring was continued at room temperature overnight. The DMF was removed under reduced pressure and the resulting mixture was poured into 350 ml ethyl acetate. The ethyl acetate solution was washed by H$_2$O, saturated NaHCO$_3$, brine, saturated NaHSO$_4$ and brine again until the pH of the brine layer was about 7. The organic layer was dried by Na$_2$SO$_4$ and the ethyl acetate was removed under reduced pressure to get the crude product. Column chromatography (elution solvents: E/H, 3:1) was carried out to obtain the pure product (17.5 g, 85%). TLC Rf=0.45 (developing solvents: E/H, 3:1).

Boc-Gly-Nleu-Pro-OH

Boc-Gly-Nleu-Pro-OBz (7.9 g, 0.0166 mol.) was dissolved in a mixture of 50 ml H$_2$O and 80 ml THF. The solution was chilled to 0° C. KOH (1.9 g, 0.033 mol.) dissolved in 30 ml H$_2$O was added while stirring the solution. The stirring was continued at room temperature for one hour. The THF was removed under reduced pressure. The aqueous solution was chilled to 0° C. and acidified to about pH=3 by addition of concentrated HCl (swirling the solution vigorously at the same time). The product was extracted from the aqueous solution by ethyl acetate. The combined organic layer was dried using Na$_2$SO$_4$ and the ethyl acetate was removed under reduced pressure to obtain the product (5.7 g, 89%). TLC Rf=0.38 (developing solvents: CMA, 85:15:3). FAB-MS, observed (M+H)$^+$=386. $^1$H-NMR (500 MHz, DMSO-d6, 27° C., assignment by TOCSY) δ 6.69 (m, Gly-NH), 6.57 (m, Gly-NH), 4.56 (m, Pro-α), 4.28–4.14 (m, Pro-α), 4.14–3.97 (m, Nleu-α), 3.83–3.62 (m, Gly-α), 3.62–3.44 (m, Gly-α, Pro-δ), 3.44–3.28 (m, Pro-δ), 3.12–2.92 (m, Nleu-β), 2.23–1.58 (m, Pro-β, Pro-γ, Nleu-γ), 1.34 (m, Boc-CH$_3$), 0.85 (m, Nleu-δ), 0.78 (m, Nleu-δ).

EXAMPLE 7

Synthesis of Chains of Sequential Peptoid Residue Containing Trimers:

(Gly-Pro-Nleu)$_n$—NH$_2$

Boc-Gly-Pro-Nleu-NH$_2$

Boc-Gly-Pro-Nleu-OH (4.1 g, 0.0106 mol.), NH$_4$Cl (1.7 g, 0.032 mol.) and HOBt (1.76 g, 0.013 mol.) were dissolved in 100 ml DMF and the solution was chilled to 0° C. TEA (4.5 ml) was added to the solution slowly while stirring the solution. After a while, EDC (2.6 g, 0.013 mol.) was added to the solution. The stirring was continued overnight. The DMF was removed under reduced pressure and the resulting mixture was poured into 350 ml chloroform. The chloroform solution was washed by H$_2$O 2×20 ml, saturated NaHCO$_3$ 2×20 ml, brine 2×20 ml, saturated NaHSO$_4$ 2×20 ml and brine again until the pH of the brine layer was approximate 7. The organic layer was dried using Na$_2$SO$_4$ and the chloroform was distilled under reduced pressure to obtain the product (3.5 g, 84%). TLC Rf=0.36 (developing solvents: CMA, 85:15:3).

Gly-Pro-Nleu-NH$_2$

Boc-Gly-Pro-Nleu-NH$_2$ (3.5 g, 0.0089 mol.) was dissolved in a solution of 30% TFA in DCM (50 ml). The solution was stirred for 40 minutes. The DCM and TFA were removed under reduced pressure, and 3×50 ml benzene were added and distilled under reduced pressure to remove trace TFA. The resulting mixture was dissolved in 30 ml methanol and the solution was chilled to 0° C. HCl/dioxane (4N, 10 ml) was added to the solution to transfer the product from TFA salt to HCl salt. Ethyl ether (200 ml) was added to the solution and a precipitation formed. The ether was removed by filtration and a white solid product was obtained (2.9 g, 87%). Analytical RP-HPLC chromatogram, single peak, RT=15.7 min. (5–15% B in 30 min.). FAB-MS, observed (M+H)$^+$=285. $^1$H-NMR (500 MHz, DMSO-d6, 25° C., assignment by TOCSY) δ 8.03 (m, 3H, Gly-NH$_3$), 7.65 (s, C-terminal NH$_2$), 7.46 (s, C-terminal NH$_2$), 7.34 (s, C-terminal NH$_2$), 7.24 (d, C-terminal NH$_2$), 7.08 (s, C-terminal NH$_2$), 6.92 (s, C-terminal NH$_2$), 4.94 (d, Pro-α), 4.76 (m, Pro-α), 4.59 (m, Pro-α), 4.25–3.52 (sets of bands, Nleu-α, Gly-α), 3.52–3.44 (m, Pro-δ), 3.42–2.70 (sets of bands, Gly-α, Nleu-β), 2.36–1.65 (sets of bands, Pro-β, Pro-γ, Nleu-γ), 0.90 (m, Nleu-δ), 0.79 (m, Nleu-δ).

(Gly-Pro-Nleu)$_2$—NH$_2$

Boc-Gly-Pro-Nleu-OH (0.3 g, 0.76 mmol.) and Gly-Pro-Nleu-NH$_2$ (0.00075 mol.) were dissolved in 20 ml DMF and the solution was chilled to 0° C. TEA (0.3 ml) was added slowly while stirring the solution. After 10 minutes, BOP (0.5 g, 0.0012 mol.) was added to the solution and the stirring was continued overnight. The DMF was removed and the resulting mixture was poured into 150 ml chloroform. The chloroform solution was washed by H$_2$O 2×10 ml, saturated NaHCO$_3$ 2×10 ml, brine 2×10 ml, saturated NaHSO$_4$ 2×10 ml and brine again until the pH of the brine layer was approximate 7. The organic layer was dried using Na$_2$SO$_4$ and the chloroform was distilled under reduced pressure to obtain the Boc-(Gly-Pro-Nleu)$_2$—NH$_2$. This product was dissolved in a solution of 30% TFA in DCM (30 ml) and the solution was stirred at room temperature for 30 minutes. The DCM and TFA were removed under reduced pressure, and 3×20 ml benzene were added and distilled under reduced pressure to remove trace TFA. The crude product was dissolved in water and HPLC was carried out to obtain the pure product (white solid, 0.25 g, 60%). FAB-MS, observed (M+H)$^+$=552. Analytical HPLC chromatogram, single peak, RT=9.3 min. (10–30% B in 30 min.).

(Gly-Pro-Nleu)$_3$—NH$_2$ (Gly-Pro-Nleu)$_3$-MBHA (0.2 mmol based on the resin substitution) was obtained using the general solid phase synthesis procedures described in the General Information section. The peptide-peptoid residue was removed from the resin by the HF cleavage method using anisol (1 ml) as the scavenger. The HF cleavage proceeded one hour at –5° C. to 0° C. After the HF cleavage, the product and resin mixture was washed several times by anhydrous ethyl ether on a sintered glass filter and the product was separated from the resin by extraction with a mixture of H$_2$O and CH3CN. Lyophilizing was performed to get the crude product and HPLC was carried out to obtain the pure product (90 mg, 55%). FAB-MS, observed (M+H)$^+$=819. Analytical HPLC chromatogram, single peak, RT=15.8 min. (15–60% B in 30 min.).

(Gly-Pro-Nleu)$_n$—NH$_2$ (n=4, 5, 6, 7, 9)

The synthesis, purification and characterization of these compounds were similar to that of (Gly-Pro-Nleu)$_3$—NH$_2$.

EXAMPLE 8

Synthesis Chains of Sequential Peptoid Residue-Containing Trimer Chains: Ac-(Gly-Pro-Nleu)$_n$,—NH$_2$ Ac-Gly-Pro-Nleu-NHCH$_3$ Boc-Gly-Pro-Nleu-OH (0.77 g, 2 mmol), HClNH$_2$CH$_3$ (0.27 g, 4 mmol.) and HOBt (0.35 g, 2.5 mmol) were dissolved in DMF and the solution was chilled to 0° C. on a water-ice bath. Triethylamine (0.7 ml) was added slowly while stirring the solution. After 5 minutes, EDC (0.46 g, 2.4 mmol.) was added to the solution and the stirring continued overnight. The DMF was removed under reduced pressure and the resulting mixture was poured into 150 ml chloroform. The chloroform solution was washed by H$_2$O, saturated NaHCO$_3$, brine, saturated NaHSO$_4$ and brine again until the pH of the brine layer was approximate 7. The organic layer was dried using Na$_2$SO$_4$ and the chloroform was distilled under reduced pressure to obtain the Boc-Gly-Pro-Nleu-NHCH$_3$. TLC Rf=0.44 (developing solvents: CMA, 85:15:3). This product was used directly in next step without further purification and characterization. 30 ml solution of 30% TFA in DCM was used to remove the Boc group. The deprotection was allowed to proceed 30 minutes. Then, the DCM and TFA was removed under reduced pressure and benzene 3×20 ml was added and distilled to remove trace TFA. The TFA salt of Gly-Pro-Nleu-NHCH$_3$ was dissolved in 50 ml and the solution was chilled to 0° C. Triethylamine was added slowly to neutralize the peptide. After a while, acetic anhydride (2ml) was added and the acetylation was allowed to proceed 40 minutes. The DCM was removed and the resulting mixture was dissolved in 100 ml chloroform. The chloroform solution was washed by H$_2$O, saturated NaHCO$_3$, brine, saturated NaHSO$_4$ and brine again until the pH of the brine layer was approximately 7.

The organic layer was dried using $Na_2SO_4$ and the chloroform was distilled under reduced pressure to obtain the final product Ac-Gly-Pro-Nleu-$NHCH_3$ (0.6 g, 88%). Analytical HPLC profile, single peak, RT=10.5 min. (10–50% B in 30 min.). FAB-MS, observed $(M+H)^+$=341. $^1$-NMR (500 MHz, DMSO-d6, 28° C., assignment by TOCSY) δ 8.04 (m, C-terminal NH), 7.93 (m, Gly-NH), 7.71 (m, C-terminal NH), 7.48 (m, C-terminal NH), 4.94 (d, Pro-α), 4.81 (m, Pro-α), 4.68 (m, Pro-α), 4.50 (m, Pro-α), 4.29–3.52 (sets of bands, Nleu-α, Gly-α), 3.52–3.42 (m, Pro-δ), 3.36 (m, Pro-δ), 3.29–2.86 (sets of bands, Nleu-β), 2.59 (m, C-terminal N-$CH_3$), 2.53 (m, C-terminal N-CH3), 2.31–2.03 (sets of bands, Pro-β), 1.96 (m, Pro-β, Pro-γ), 1.92–1.61 (m, acetyl-$CH_3$, Pro-β, Nleu-g, Pro-γ), 0.86 (dd, Nleu-δ), 0.75 (m, Nleu-δ).

Ac-(Gly-Pro-Nleu)$_6$—$NH_2$

Ac-(Gly-Pro-Nleu)$_6$-MBHA (0.45 mmol. based on the resin substitution) was obtained using the solid phase synthesis procedures described in the General Information section. After HF cleavage, lyophilizing was performed to get the crude product and HPLC was carried out to obtain the pure product (47%). FAB-MS, observed $(M+H)^+$=1663. Analytical HPLC chromatogram, single peak, RT=18.2 min. (15–80% B in 30 min.).

Ac-(Gly-Pro-Nleu)$_9$—$NH_2$

The synthesis, purification and characterization of this compound was similar to that of Ac-(Gly-Pro-Nleu)$_6$—$NH_2$. Physicochemical data for the synthetic peptide peptoid residue compounds composed of Gly-Pro-Nleu sequences are given below in Table 2.

TABLE 2

Physicochemical data for the synthetic peptide-peptoids composed of Gly—Pro—Nleu sequences

| Compounds | MW | MS results | HPLC RT (min)[a] | Yields[b] |
|---|---|---|---|---|
| Ac—Gly—Pro—Nleu—$NH_2$[c] | 326 | $MH^+$, 327 (FAB) | 12.2<br>10–20% B, 30 min. | 59% |
| Ac—Gly—Pro—Nleu—$NHCH_3$[c] | 340 | $MH^+$, 341 (FAB) | 10.5<br>10–50% B, 30 min. | 88% |
| Ac—(Gly—Pro—Nleu)$_6$—$NH_2$ | 1663 | $MH^+$, 1663 (FAB) | 18.2<br>15–80% B, 30 min. | 47% |
| Ac—(Gly—Pro—Nleu)$_9$—$NH_2$ | 2465 | $MNa^+$, 2488 (FAB) | 14.8<br>30–90% B, 30 min | 29% |
| Gly—Pro—Nleu—$NH_2$[c] | 284 | $MH^+$, 285 (FAB) | 15.7<br>5–15% B, 30 min. | 87% |
| (Gly—Pro—Nleu)$_2$—$NH_2$[c] | 552 | $MH^+$, 552 (FAB) | 9.3<br>10–30% B, 30 min. | 60% |
| (Gly—Pro—Nleu)$_3$—$NH_2$ | 819 | $MH^+$, 819 (FAB) | 15.8<br>15–60% B, 30 min. | 55% |
| (Gly—Pro—Nleu)$_4$—$NH_2$ | 1086 | $MH^+$, 1086 (FAB) | 11.2<br>30–50% B, 30 min. | 61% |
| (Gly—Pro—Nleu)$_5$—$NH_2$ | 1354 | $MH^+$, 1354 (FGAB) | 14.4<br>30–50% B, 30 min. | 37% |
| (Gly—Pro—Nleu)$_6$—$NH_2$ | 1621 | $MH^+$, 1621 (FAB) | 16.5<br>10–50% B, 30 min. | 37% |
| (Gly—Pro—Nleu)$_7$—$NH_2$ | 1888 | $MH^+$, 1889 (ESI) | 18.6<br>15–85% B, 30 min. | 45% |
| (Gly—Pro—Nleu)$_9$—$NH_2$ | 2423 | $MH^+$, 2425 (FAB) | 20.7<br>10–50% B, 30 min. | 61% |

[a]Vydac C-18 column, 0.46 × 25 cm, flow rate: 1.0 ml/min.
[b]For those compounds prepared by solid phase methods, the yields were calculated based on the resin substitutions and the materials obtained from HPLC purification.
[c]Prepared by solution peptide synthesis methods.

Ac-Gly-Pro-Nleu-$NH_2$

HCl-Gly-Pro-Nleu-$NH_2$ (0.32 g, 0.001 mol.) was dissolved in 5 ml DCM and the solution was chilled to 0° C. 0.3 ml diisopropylethylamine (DIEA) was added to the solution slowly. After a while, acetic anhydride (0.3 ml) was added while stirring the solution. The stirring was continued for one hour at room temperature. The DCM was removed under reduced pressure and the resulting mixture was dissolved in $H_2O$. RP-HPLC was carried out to obtain the pure product (210 mg, 59%). FAB-MS, observed $(M+H)^+$=327. Analytical HPLC, single peak, RT=12.2 min. (10–20% B in 30 min.). $^1$H-NMR (500 MHz, DMSO-d6 assignment by TOCSY) δ 7.97 (m, 1H, Gly-NH), 7.52 (m, 0.5H, C-terminal $NH_2$), 7.22 (m, 0.5H, C-terminal $NH_2$), 7.05–6.80 (m, 1H, C-terminal $NH_2$), 4.94 (d, 0.11H, Pro-α), 4.78 (, 0.16H, Pro-α), 4.69 (d, 0.41H, Pro-α), 4.51 (d, 0.32H, Pro-α), 4.18 (d, 0.35H, Nleu-α), 4.05–3.60 (m, Gly-α, Nleu-α), 3.56–2.90 (m, Gly-α, Nleu-β, Pro-δ), 2.60–1.40 (m, Pro-γ, Pro-δ, Nleu-γ), 0.87 (dd, Nleu-δ methyl), 0.76 (dd, Nleu-δ methyl).

The polypeptides composed of the Gly-Pro-Hyp and Gly-Pro-Pro sequences were prepared as references to establish the triple helical propensity of the collagen-like poly (peptide-peptoid residue) structures.

Preparation of the Following Polypeptides:

(Ala-Sar-Gly)$_n$ (Ala-Nphe-Gly)$_n$ (Gly-Sar-Ala)$_n$ (Glu-Sar-Gly)$_n$ (Gly-Pro-Sar)$_n$ (Lys-Sar-Gly)$_n$ are reported by Goodman, M. et al. (1994) Polymer Preprint 35(1):767–768.

Mass spectra and NMR were used to verify the structures. The yields were calculated based on the resin substitution and the materials obtained after HPLC purification.

EXAMPLE 9

Synthesis of Template-Spacer KTA-(Gly-OH)$_3$
KTA-(Gly-OBz)$_3$

The Kemp triacid (KTA) (0.1, g, 0039 mol.) TOS-Gly-OBz (6.5 g, 0.019 mol.) and HOBt (2.6 g, 0.019 mol.) were dissolved in 50 ml DMF. The solution was chilled to 0° C. and TEA (5 ml, 0.036 mol.) was added slowly. After stirring the solution for 5 minutes, EDC (3.7 g, 0.019 mol.) was added. The reaction continued 4 hours at room temperature. The DMF was distilled under reduced pressure and the remaining mixture was poured into 300 ml ethyl acetate. The ethyl acetate solution was washed by general procedures ($H_2O$, saturated $NaHCO_3$, brine, saturated $NaHSO_4$ and brine again until neutral) and dried by $Na_2SO_4$. The solvent was removed to get the crude product. Column chromatography (elution solvents: ethyl acetate/hexane, E/H, 3:2) was carried out to obtain KTA-(Gly-OBz)$_3$(white oil, 2.65 g, 97.8%). TLC Rf=0.55 (E/H, 3:1).

KTA-(Gly-OH)$_3$

The KTA-(Gly-OBz)$_3$ (2.65 g, 0.0038 mol.) was dissolved in 200 ml methanol. After bubbling $N_2$ into the solution for 10 minutes to remove the dissolved air, 10% Pd/C (0.2 g) was added. Hydrogen was led to the solution and hydrogenolysis was continued until the consumption of hydrogen stopped. The catalyst was removed by filtration and the solvent methanol was removed under reduced pressure to give a pure product (white solid, 1.55 g, 97% yield). TLC Rf=0.05 (CMA, 85:15:3). The analytical HPLC profile showed a single homogeneous peak with RT=14 minute (0.1% TFA in the elution solvents, 10–30% B, 30 minutes). FAB-MS, observed (M+H)$^+$=430. $^1$H-NMR (360 MHz, DMSO-d$_6$, 20° C.) δ 7.93 (s, 3H, NH), 3.64 (s, 6H, Gly-α), 2.54 (d, 3H, CH$_2$-equatorial), 1.24–1.18 (m, 12H, 9H for CH$_3$ and 3H for CH$_2$-axial).

EXAMPLE 10

Synthesis of Template-Spacer KTA-(aha-OH)$_3$ 6-aminohexanoic acid benzyl ester Aha-OBz 6-aminohexanoic acid (Aha-OH) (13.1 g, 0.1 mol), benzyl alcohol (100 mL), benzene (100 mL) and tolylsulfonic acid (19 g, 0.1 mol) were mixed and the mixture was refluxed for 3 h using a Dean Stark apparatus. The resulting mixture was cooled to room temperature and 500 mL ethyl ether was added. The precipitate was collected by filtration and washed using ethyl ether and dried in vacuum overnight to get a white solid product Tos-Aha-OBz (40.5 g, 98%).

KTA-(Aha-OBz)$_3$

Kemp triacid (1.0 g, 0,00387 mol), Tos-Aha-OBz (8.0 g, 0.0194 mol) and HOBt (2.6 g, 0.0194 mol) were dissolved in DMF (50 ml) and the solution was chilled to 0° C. TEA (5 mL) was added to the solution portionwise. After stirring the solution for 10 minutes, EDC (3.7 g, 0.0194 mol) was added and the solution was stirred overnight at room temperature. The DMF was removed under reduced pressure and the resulting mixture was poured into 200 mL ethyl acetate. The ethyl acetate solution was washed by $H_2O$ (2×30 mL), saturated $NaHCO_3$ (3×15 mL), brine (2×10 mL), saturated $NaHSO_4$ (3×15 mL) and brine again until the pH of the brine layer was approximate 7. The organic layer was dried over anhydrous $Na_2SO_4$ and the ethyl acetate was removed by distillation under reduced pressure. Column chromatography (elution solvents: E/H, 3:1) was carried out to obtain the pure product (white solid, 3.4 g, 89%). TLC Rf=0.56 (developing solvents: E/H, 3:1). $^1$H-NMR (360 MHz, DMSO-d6, 20° C.) δ 7.84 (m, 3H, NH), 7.52 (m, 15H, phenyl), 5.26 (s, 6H, benzyl CH$_2$), 3.12 (m, 6H, (-CH$_2$), 2.77 (d, 3H, equatorial KTA-CH$_2$), 2.49 (t, 6H, α-CH$_2$), 1.70 (m, 6H, δ-CH$_2$), 1.53 (m, 6H, β-CH$_2$), 1.42 (b, 6H, γ-CH$_2$), 1.29 (m, 12H, KTA-CH$_3$ and axial KTA-CH$_3$).

KTA-(Aha-OH)$_3$

KTA-(Aha-OBz)$_3$ (3.0 g, 0.0035 mol) was dissolved in methanol (100 mL). Pd/C (10% about 0.3 g) was added to the solution carefully. The solution was placed under H$_2$ overnight at room temperature. The Pd/C was removed by filtration and the methanol was removed under reduced pressure. A white solid was obtained (2.0 g, 96%). TLC Rf=0.27 (developing solvents: CMA, 85:15:3). FAB MS, observed (M+H)$^+$=599. Analytical RP-HPLC, homogeneous single peak, RT=15 min (25–50% B in 30 min). $^1$H-NMR (360 MHz, DMSO-d6, 20° C.) δ 12.0 (s, 3H, carboxyl), 7.63 (m, 3H, NH), 2.93 (m, 6H, (-CH$_2$), 2.57 (d, 3H, equatorial KTA-CH$_2$), 2.16 (t, 6H, α-CH$_2$), 1.47 (m, 6H, δ-CH$_2$), 1.34 (m, 6H, β-CH$_2$), 1.24 (m, 6H, γ-CH$_2$), 1.10 (m, 12H, KTA-CH$_3$ and axial KTA-CH$_2$).

EXAMPLE 11

Synthesis of the TMA Template-Spacer TMA-(Gly-OBz)$_3$

Tos-Gly-OBz (8.4 g, 0.025 mol) was dissolved in DCM (150 mL) and the solution was chilled to 0° C. TEA (5 mL) was added slowly. After 10 minutes, trimesic acid chloride (1.4 g, 0.005 mol) was added and the solution was stirred at room temperature for 5 h. DCM was removed under reduced pressure and the resulting mixture was poured into 300 mL ethyl acetate. The ethyl acetate solution was washed with $H_2O$ (2×30 mL), saturated $NaHCO_3$ (3×15 mL), brine (2×10 mL), saturated $NaHSO_4$ (3×15 mL) and brine again until the pH of the brine layer was approximate 7. The organic layer was dried over anhydrous $Na_2SO_4$ and the ethyl acetate was removed by distillation under reduced pressure. A white solid was obtained (2.4 g, 74%). TLC Rf=0.54 (developing solvents: E/H, 3:1). $^1$H-NMR (360 MHz, DMSO-d6, 20° C.) δ 9.18 (m, 3H, NH), 8.43 (s, 3H, benzene), 7.18 (m, 15H, phenyl), 5.11 (s, 6H, benzyl), 4.05 (m, 6H, glycine α-CH$_2$).

TMA-(Gly-OH)$_3$

TMA-(Gly-OBz)$_3$ (2.4 g, 0.0035 mol) was dissolved in a solution of 10% DMF in methanol (150 mL). Pd/C (10%, about 0.3 g) was added to the solution and the solution was placed under H2. After 3 h, the Pd/C was removed by filtration and the solvents were removed under reduced pressure. Ether (50 mL) was added and the precipitate was collected by filtration. A white solid product was obtained (1.4 g, 100%). FAB MS, observed (M+H+NH$_3$)$^+$=399. $^1$H-NMR (360 MHz, DMSO-d6, 20° C.) δ 12.57 (s, 3H, carboxyl), 9.00 (m, 3H, NH), 8.43 (s, 3H, benzene), 3.91 (m, 6H, glycine α-CH$_2$).

EXAMPLE 12

Synthesis of the KTA Template-Assembled Collagen-like Structures

KTA-[Gly-Gly-Pro-Nleu-NH$_2$]$_3$

KTA-(Gly-OH)$_3$ (0.11 g, 0. 25 mmol), HCl•Gly-Pro-Nleu-NH$_2$ (0.4 g, 1.25 mmol) and HOBt (0.14 g, 1.0 mmol) were dissolved in DMF (5 mL) and the solution was chilled to 0° C. TEA (0.2 mL) was added slowly. After 10 minutes, EDC (0.19 g, 1.0 mmol) was added and the stirring was continued overnight at room temperature. DMF was removed under reduced pressure and the resulting mixture was dissolved in water. Dialysis was performed in a membrane tubing with cut-off of 1000 dalton for one day to remove low molecular weight impurities. A crude product was obtained after lyophilization and HPLC was carried out to obtain the pure product (0.25 g, 80%). FAB MS, observed (M+H)$^+$=1229. Analytical HPLC chromatogram, homogeneous single peak, RT=18.7 min (30–70% B in 25 min). $^1$H-NMR (500 MHz, DMSO, 23° C., assignment by 2-D TOCSY) δ 8.22 (m, 3H, spacer Gly-NH), 7.85–7.70 (m, 2 sets, 3H, Gly-NH), 7.60–6.85 (4 sets, 6H, C-terminal NH$_2$), 4.95–4.45 (4 sets, 3H, Pro-α), 4.22 (d, 1H, Nleu-α), 4.10–3.70 (m, Gly-α, Nleu-α), 3.70–3.30 (m, covered by water signal, spacer Gly-α, Gly-α, Pro-δ, Nleu-α), 3.28–2.81 (sets of bands, Nleu-β), 2.64 (d, 3H, equatorial KTA-CH$_2$), 2.36–1.60 (sets of bands, Pro-β, Pro-γ, Nleu-γ), 1.14 (s, 9H, KTA-CH$_3$), 1.07 (d, 3H, axial KTA-CH$_2$), 0.88 (dd, Nleu-δ), 0.78 (dd, Nleu-δ).

KTA-[Gly-(Gly-Pro-Nleu)$_3$—NH$_2$]$_3$ (Gly-Pro-Nleu)$_3$-MBHA (0.45 mmol based on the resin substitution), which was obtained using the general solid phase synthesis procedures described in the General Information section, was put in a solid phase reaction vessel. KTA-(Gly-OH)$_3$ (58 mg, 0.135 mmol) was added to the vessel and the coupling reaction was initiated using DIC and HOBt as the coupling reagents and DMF/DCM (v/v, 1:4) as the solvents. More DIC was added after one day and the coupling reaction was allowed to proceed for two days, at which point the Kaiser test showed no more free amine. After HF cleavage, 255 mg crude material was obtained. HPLC was carried out to obtain the pure product (65 mg, 6%). MALDI MS, observed (M+Na)+=2852. Analytical HPLC chromatogram, homogeneous single peak, RT=15.2 min (30–90% B in 30 min)

KTA-[Gly-(Gly-Pro-Nleu)$_6$—NH$_2$]$_3$

The solid phase method: (Gly-Pro-Nleu)$_6$-MBHA (0.3 mmol based on the resin substitution) was obtained using the general solid phase synthesis procedures described in the General Information section. KTA-(Gly-OH)$_3$ (30 mg, 0.07 mmol) was coupled to the N-termini of the peptide-peptoid residue chains using DIC and HOBt as the coupling reagents and DMF/DCM (v/v, 1:1) as the solvents. Two couplings were performed to ensure complete functionalization. For the first coupling, 0.035 mmol template was used and the coupling was allowed to proceed for one day. The solution was removed from the reaction vessel by filtration and the resin was washed with DCM (3×20 mL). Another 0.035 mmol template was used for a second coupling which was allowed to proceed for two days. More DIC was added after one day in the second coupling. After the three days and two couplings, the Kaiser test showed no more free amine. The HF cleavage method was used to removed the peptide-peptoid residue from the resin. Lyophilization gave a crude product (245 mg) and HPLC was carried out to obtain the pure product (14%). The solution method (Gly-Pro-Nleu)$_6$—NH$_2$ (166 mg, 0.1 mmol) which was obtained using the general solid phase synthesis procedures described in the General Information section and KTA-(Gly-OH)$_3$ (14.5 mg, 0.033 mmol) was dissolved in DMF (2 mL). The solution was chilled to 0° C. and TEA (0.03 mL) was added while stirring the solution. After 5 minutes, BOP (75 mg, 0.17 mmol) was added to the solution and the coupling reaction was allowed to proceed for 18 h at room temperature. The solvent was removed under reduced pressure and the resulting mixture was dissolved in H$_2$O (25 mL). The aqueous solution was dialyzed against water in a 3500 dalton cut-off membrane tubing for 10 h to remove low molecular weight impurities. Lyophilization gave the crude product and HPLC was carried out to obtain the pure product (35 mg, 21%). ESI MS, observed (M+H)+=5238. Analytical HPLC chromatogram, single peak, RT=13.4 min (35–90% B in 30 min)

KTA-[Gly-(Gly-Pro-Nleu)$_9$—NH$_2$]$_3$ (Gly-Pro-Nleu)$_9$—NH$_2$ (400 mg, 0.164 mmol) which was obtained using the general solid phase synthesis procedures described in the General Information section, KTA-(Gly-OH)$_3$ (23.5 mg, 0.055 mmol) and HOBt (22 mg, 0.164 mmol) were dissolved in DMF (3 mL). The solution was chilled to −50° C. and TEA (0.02 mL) was added. After 5 minutes, EDC (38 mg, 0.2 mmol) was added and the solution was stirred at −50 to −20° C. for 2 h. The dry ice-isopropanol bath was removed and the solution was stirred overnight at room temperature. The solution was chilled to 0° C. and BOP (50 mg, 0.11 mmol) was added. TEA was added to adjust the pH of the solution to about 9. The solution was stirred at room temperature for three more days. The DMF was removed under reduced pressure and the resulting mixture was dissolved in a mixture of acetonitrile and water and dialyzed against water in a 3500 dalton cut-off membrane tubing for three days. Lyophilization gave the crude product (330 mg) and HPLC was carried out to obtain the pure product (43 mg, 10%). ESI MS, observed (M+H)+=7645. Analytical HPLC chromatogram, single peak, RT=14.2 min (50–90% B in 30 min).

KTA-[Aha-(Gly-Pro-Nleu)$_6$—NH$_2$]$_3$ (Gly-Pro-Nleu)$_6$-MBHA (0.45 mmol based on the resin substitution) was obtained using the general solid phase synthesis procedures described in the General Information section. KTA-(Aha-OH)$_3$ (65 mg, 0.1086 mmol) was coupled to the N-termini of the peptide-peptoid residue chains as described for the synthesis of KTA-[Gly-(Gly-Pro-Nleu)$_6$—NH$_2$]$_3$. After the HF cleavage, lyophilization gave the crude product (200 mg) and HPLC was carried out to obtain the pure product (53 mg, 9%). ESI MS, observed (M+H)+=5407. Analytical HPLC chromatogram, single peak, RT=13.9 min (35–90% B in 30 min).

KTA-[Gly-(Gly-Nleu-Pro)$_3$—NH$_2$]$_3$ (Gly-Nleu-Pro)$_3$-MBHA (0.35 mmol based on the resin substitution) was obtained using the solid phase synthesis procedures described in the General Information section. The template KTA-(Gly-OH)$_3$ (45 mg, 0.105 mmol) was coupled to the N-termini of the peptide-peptoid chains using DIC and HOBt as the coupling reagents and DMF/DCM (v/v, 1:4) as the solvents. The coupling was allowed to proceed one day and the Kaiser test showed the complete consumption of the peptide-peptoid free amine. The HF cleavage method and work-up procedures as described in the General Information section was used to obtain the crude product and HPLC was carried out to obtain the pure product (20 mg, 6%). Analytical RP-HPLC chromatogram, single peak, RT=16.1 min (25–70% B 30 min). MALDI MS, observed (M+Na)+=2855.

KTA-[Gly-(Gly-Nleu-Pro)$_6$—NH$_2$]$_3$ (Gly-Nleu-Pro)$_6$-MBHA (0.5 mmol based on the resin substitution) was obtained using the solid phase synthesis procedures described in the General Information section. The template KTA-(Gly-OH)$_3$ (totally 56 mg, 0.131 mmol) was coupled to the N-termini of the peptide-peptoid chains by two consecutive couplings using DIC and HOBt as the coupling reagents and DMF/DCM (v/v, 1:4) as the solvents. For the first coupling, 36 mg (0.084 mmol) KTA-(Gly-OH)$_3$ was used. The coupling was allowed to proceed one day. The mixture was filtered and another 20 mg (0.047 mmol) KTA-(Gly-OH)$_3$ was used (with coupling reagents DIC and HOBt) for a second coupling. This second coupling was also allowed to proceed one day. The template-assembled peptide-peptoid product was removed from the resin by the HF cleavage method and was dialyzed against water in a 3500 dalton cut-off membrane tubing for 3 days. HPLC was carried out to obtain the pure proudct (30 mg, 4.4%), A product with two chains attached to the template was also obtained. MALDI MS, observed (M+Na)+=5259. Analytical HPLC chromatogram, RT=14.3 min. (35–70% B, 30 min).

EXAMPLE 13

Synthesis of the TMA Template-Assembled Collagen-like Structures

TMA-[Gly-Gly-Pro-Nleu-NH$_2$]$_3$

TMA-(Gly-OH)$_3$ (0.1 g, 0.25 mmol), HCl(Gly-Pro-Nleu-NH$_2$ (0.26 g, 0.85 mmol) and HOBt (0.14 g, 1.0 mmol) were dissolved in DMF (3 mL) and the solution was chilled to 0° C. TEA (0.2 mL) was added slowly while stirring the solution. After 10 minutes, EDC (0.19 g, 1.0 mmol) was added and the stirring was continued overnight at room temperature. The DMF was removed under reduced pressure and the resulting mixture was dissolved in water. Dialysis was performed in a membrane tubing with cut-off of 1000 dalton for 9 hours to remove low molecular weight impurities. Lyophilization gave the crude product (0.29 g) and HPLC was carried to obtain the pure product (113 mg, 38%). FAB MS, observed (M+Na)$^+$=1203. Analytical HPLC chromatogram, single peak, RT=15.9 min. (30–70% B in 30 min). $^1$H-NMR (500 MHz, DMSO, 23° C., assignment by 2-D TOCSY) δ 8.94 (m, 3H, template spacer Gly NH), 8.48 (s, 3H, benzene), 8.05 (m, 3H, Gly NH), 7.60–6.80 (4 sets of signals, 6H, C-terminal NH$_2$), 4.95–4.50 (4 sets of signals, 3H, Pro-α), 4.20 (d, 1H, Nleu-α), 4.10–3.70 (m, 16H, spacer Gly-α, Gly-α, Nleu-α), 3.63 (d, 2H, Nleu-α), 3.55–2.85 (m, Gly-α, Pro-δ, Nleu-β), 2.40–1.60 (m, Pro-δ, Pro-γ, Nleu-γ), 0.88 (dd, Nleu-δ), 0.76 (dd, Nleu-δ).

TMA-[Gly-(Gly-Pro-Nleu)$_6$—NH$_2$]$_3$

(Gly-Pro-Nleu)$_6$-MBHA (0.3 mmol based on the resin substitution) was obtained using the solid phase synthesis procedures described in the General Information section. The template TMA-(Gly-OH)$_3$ was coupled to the N-termini using DIC and HOBt as the coupling reagents and DMF/DCM (v/v, 1:1) as the solvent. Two couplings were used to ensure high yields of the target 3-chain product (see the General Information section). In the first coupling, 0.035 mmol TMA-(Gly-OH)$_3$ was used. After one day, the solution was filtered and the resin was washed by DCM (3×20 mL). A positive Kaiser test result was observed and another 0.035 mmol TMA-(Gly-OH)$_3$ was used for a second coupling. The coupling was continued 24 h at which point the Kaiser test showed no more free amine. Thus, a total of 0.07 mmol template was used to couple with 0.3 mmol (Gly-Pro-Nleu)$_6$-MBHA. The peptide-peptoid was removed from the resin by the HF cleavage method and HPLC was carried out to obtain the pure product (35 mg, 10%) ESI MS, observed (M+H)$^+$=5190. Analytical HPLC chromatogram, single peak with RT=15.9 min. (40–95% B in 30 min)

TMA-[(Gly-Pro-Nleu)$_9$—NH$_2$]$_3$

(Gly-Pro-Nleu)$_9$—NH$_2$ (74 mg, 0.03 mmol), which was obtained using the solid phase synthesis procedures described in the General Information section, was dissolved in DCM (2 mL) and the solution was chilled to 0° C. Trimesic acid chloride (2.7 mg, 0.01 mmol) was added and after 5 minutes, triethylamine (0.1 mL) was added to the solution and the reaction was stirred overnight at room temperature. The DCM was removed under reduced pressure and the resulting mixture was dissolved in a mixture of H$_2$O and CH3CN. This solution was dialyzed against water in a membrane tubing with a 3500 dalton cut-off for 3 days. The bath water was replaced every 4–8 h. Lyophilization gave the crude product (65 mg) and HPLC was carried out to obtain the pure product (15 mg, 20%). ESI MS, observed (M+H)$^+$=7424. Analytical HPLC chromatography, RT=18 min. (35–90% B in 30 min).

After the products were purified by HPLC, their purity was checked by analytical HPLC profiles. Mass spectra were used to verify the structures. The yields were calculated based on the resin substitution level and the pure products obtained after HPLC purification.

The following compounds were synthesized using one or both of the above two synthetic routes:

KTA—[Gly—(Gly—Pro—Nleu)$_n$—NH$_2$]$_3$    (n = 1, 3, 6, 9)
KTA—[Gly—(Gly—Nleu—Pro)$_n$—NH$_2$]$_3$    (n = 1, 3, 6, 9)
KTA—[Aha—(Gly—Pro—Nleu)$_6$—NH$_2$]$_3$    Aha denotes 6-aminohexanoic acid residue
KTA—[Gly—(Gly—Pro—Hyp)$_n$—NH$_2$]$_3$    (n = 1, 3, 5, 6)
TMA—[Gly—(Gly—Pro—Nleu)$_n$—NH$_2$]$_3$    (n = 1, 6)

(where the Gly and Aha residues attached to the templates represent spacers to which the peptide-peptoid building blocks were attached).

Physicochemical data for the synthetic template-assembled compounds is shown below in Table 3.

TABLE 3

Physicochemical data for the synthetic template-assembled compounds

| Compounds | MW | MS results | HPLC RT (min)* | Yields |
|---|---|---|---|---|
| KTA—[Gly—Gly—Pro—Nleu—NH$_2$]$_3$[a] | 1228 | MH$^+$, 1229 (FAB) | 18.7<br>30–70% B, 25 min | 80% |
| KTA—[Gly—(Gly—Pro—Nleu)$_3$—NH$_2$]$_3$[b] | 2832 | MNa$^+$, 2852 (MALDI) | 15.2<br>30–90% B, 30 min | 6% |
| KTA—[Gly—(Gly—Pro—Nleu)$_6$—NH$_2$]$_3$[a][b] | 5238 | MH$^+$, 5238 (ESI) | 13.4<br>40–95% B, 30 min | [a] 21%<br>[b] 14% |
| KTA—[Gly—(Gly—Pro—Nleu)$_9$—NH$_2$]$_3$[a] | 7644 | MH$^+$, 7645 (ESI) | 14.2<br>50–90% B, 30 min | 10% |
| TMA—[Gly—Gly—Pro—Nleu—NH$_2$]$_3$[a] | 1180 | MNa$^+$, 1203 (FAB) | 15.9<br>30–70% B, 30 min | 38% |
| TMA—[Gly—(Gly—Pro—Nleu)$_6$—NH$_2$]$_3$[b] | 5190 | MH$^+$, 5190 (ESI) | 15.9<br>35–90% B, 30 min | 10% |
| TMA—[(Gly—Pro—Nleu)$_9$—NH$_2$]$_3$[a] | 7424 | MH$^+$, 7424 (ESI) | 18.1<br>35–90% B, 30 min | 20% |
| KTA—[Aha—(Gly—Pro—Nleu)$_6$—NH$_2$]$_3$[b] | 5406 | MH$^+$, 5407 (ESI) | 13.9<br>35–90% B, 30 min | 9% |
| KTA—[Gly—(Gly—Nleu—Pro)$_3$—NH$_2$]$_3$[b] | 2832 | MNa$^+$, 2855 (MALDI) | 16.1<br>25–70% B, 30 min | 6% |

TABLE 3-continued

Physicochemical data for the synthetic template-assembled compounds

| Compounds | MW | MS results | HPLC RT (min)* | Yields |
|---|---|---|---|---|
| KTA—[Gly—(Gly—Nleu—Pro)$_6$—NH$_2$]$_3$[b] | 5238 | MNa$^+$, 5259 (MALDI) | 14.3 35–70% B, 30 min | 4.4% |

*Vydac C-18 column, 0.46 × 25 cm, flow rate: 1.0 mL/min
[a]Prepared by solution method.
[b]Prepared by solid phase method.

EXAMPLE 14

Synthesis of Peptide-Peptoid Residue Chains Composed of Gly-Nleu-Pro Sequences

Gly-Nleu-Pro-NH$_2$.

Boc-Gly-Nleu-Pro-OH (1.1 g, 2.85 mmol.), NH$_4$Cl (0.5 g, 8.6 mmol.) and HOBt (0.5 g, 3.7 mmol.) were dissolved in DMF and the solution was chilled to 0° C. on a water-ice bath. Triethylamine (1.4 ml) was added slowly while stirring the solution. After 10 minutes, EDC (0.73 g, 3.7 mmol.) was added to the solution and the stirring continued overnight. The DMF was removed under reduced pressure and the resulting mixture was poured into 300 ml ethyl acetate. The ethyl acetate solution was washed by H$_2$O 2×10 ml, saturated NaHCO$_3$ 2×10 ml, brine 2×10 ml, saturated NaHSO$_4$ 2×10 ml and brine again until the pH of the brine layer was approximate 7. The organic layer was dried using Na$_2$SO$_4$ and the ethyl acetate was distilled under reduced pressure to obtain the product Boc-Gly-Nleu-Pro-NH$_2$. The Boc group of this product was removed in 30 ml solution of 30% TFA in DCM. The deprotection reaction was allowed to proceed for 40 minutes. The DCM and TFA was removed under reduced pressure and benzene 3×20 ml was added and distilled to remove trace TFA. The product TFA salt of Gly-Nleu-Pro-NH$_2$ was dissolved in 100 ml ethyl ether and the solution was chilled to 0° C. HCl/dioxane (4N) was added to the solution until no more precipitation was seen. The ether was removed by filtration to obtain the product (white solid, 0.65 g, 69%). Analytical HPLC profile, single peak, RT=10.5 min. (8–40% B in 30 min.). FAB-MS, observed (M+H)$^+$=285. $^1$H-NMR (500 MHz, DMSO-d$_6$, 27° C., assignment by TOCSY) δ 8.15 (s, 3H, NH3+), 7.70 (s, C-terminal NH2), 7.58 (s, C-terminal NH$_2$), 7.38 (s, C-terminal NH$_2$), 7.26 (s, C-terminal NH$_2$), 7.23 (s, C-terminal NH$_2$), 6.92 (m, C-terminal NH$_2$), 4.38 (m, Pro-α), 4.30 (s, Nleu-α), 4.26 (s, Nleu-α), 4.22–4.13 (m, Nleu-α, Pro-α), 4.10 (s, Nleu-α), 4.07 (s, Nleu-α), 3.81 (m, Gly-α), 3.73–3.63 (m, Nleu-α, Gly-α), 3.61–3.55 (m, Gly-α, Pro-δ), 3.43 (m, Pro-δ), 3.17–2.97 (m, 2H, Nleu-β), 2.23–1.62 (m, 5H, Nleu-γ, Pro-β, Pro-γ), 0.83 (m, 6H, methyl of Nleu-δ).

(Gly-Nleu-Pro)$_9$—NH$_2$ (Gly-Nleu-Pro)$_9$-MBHA (0.2 mmol. based on the resin substitution) was obtained using the general solid phase synthesis procedures described in the General Information section. The peptide-peptoid was removed from the resin by the HF cleavage method using anisol as the scavenger. The HF cleavage proceeded one hour at −5° to 0° C. After the HF cleavage, the product and resin mixture was washed several times by anhydrous ethyl ether on a sintered glass filter and the product was separated from the resin by extraction with a mixture of H$_2$O and CH$_3$CN. Lyophilization gave the crude product and HPLC was carried out to obtain the pure product (90 mg, 55%). FAB-MS, observed (M+H)$^+$=2422. Analytical HPLC chromatogram, single peak, RT=15.8 min. (15–60% B in 30 min.).

Ac-(Gly-Nleu-Pro)$_3$—NH$_2$.

Boc-(Gly-Pro-Nleu)$_3$-MBHA (0.35 mmol. based on the resin substitution) was obtained using the solid phase synthesis procedures described in the General Information section. The Boc group was removed by a solution of 30% TFA in DCM. The deprotection was allowed to proceed for 30 minutes. The N-termini were acetylated using acetic anhydride (2 ml) in DCM with 5% TEA. The acetylation reaction took 30 minutes. After HF cleavage, lyophilizing was performed to get the crude product and HPLC was carried out to obtain the pure product (47%). FAB-MS, observed (M+H)$^+$=861. Analytical HPLC chromatogram, single peak, RT=15.1 min. (15–60% B in 30 min.).

Ac-Gly-Nleu-Pro-NHCH$_3$

A similar synthetic route as that of Ac-Gly-Pro-Nleu-NHCH$_3$ was used for the preparation of this compound. Boc-Gly-Nleu-Pro-OH (1.2 g, 0.31 mmol.) was used as the starting material. The final product Ac-Gly-Nleu-Pro-NHCH$_3$ (1.1 g, 91%) was obtained after C-terminal amidation, N-terminal deprotection and acetylation. Analytical HPLC profile, single peak, RT=12.2 min. (7–70% B in 30 min.). FAB-MS, observed (M+H)$^+$=341. $^1$H-NMR (360 MHz, DMSO-d6, 27° C.) d 8.05 (d, C-terminal NH), 7.98 (d, C-terminal NH), 7.90 (m, Gly-NH), 7.70 (d, C-terminal NH), 7.61 (d, C-terminal NH), 4.35 (m, Pro-α), 4.22–4.15 (m, Pro-α, Nleu-α), 4.13 (s, Nleu-α), 4.12 (s, Nleu-α), 4.10 (s, Nleu-α), 4.08 (s, Nleu-α), 4.01–3.86 (m, Gly-α, Nleu-α), 3.83 (d, Gly-α), 3.80 (d, Gly-α), 3.74 (m, Gly-α), 3.69 (d, Gly-α), 3.66 (m, Gly-α), 3.62 (s, Nleu-α), 3.60–3.30 (m, covered by water signal, Pro-δ), 3.15–2.83 (m, Nleu-β), 2.61–2.50 (m, C-terminal NCH3), 2.20–1.65 (m, Nleu-γ, Pro-β, Pro-γ), 1.82 (s, acetyl CH3), 0.85 (m, Nleu-δ), 0.77 (m, Nleu-δ). Boc-(Gly-Pro-Nleu)$_3$-MBHA (0.35 mmol. based on the resin substitution) was obtained using the solid phase synthesis procedures described in the General Information section. The Boc group was removed by a solution of 30% TFA in DCM. The deprotection was allowed to proceed for 30 minutes. The N-termini were acetylated using acetic anhydride (2 ml) in DCM with 5% TEA. The acetylation reaction took 30 minutes. After the HF cleavage, lyophilizing was performed to get the crude product and HPLC was carried out to obtain the pure product (47%). FAB-MS, observed (M+H)$^+$=861. Analytical HPLC chromatogram, single peak, RT=15.1 min. (15–60% B in 30 min.).

Ac-(Gly-Nleu-Pro)$_6$—NH$_2$ and Ac-(Gly-Nleu-Pro)$_{10}$—NH$_2$.

The synthesis, purification and characterization of these two compounds were similar to that of Ac-(Gly-Nleu-Pro)$_3$—NH$_2$.

TABLE 4

Physicochemical data for the synthetic peptide-peptoids composed of Gly—Nleu—Pro sequences

| Compounds | MW | MS results | HPLC RT (min)[a] | Yields[b] |
|---|---|---|---|---|
| Gly—Nleu—Pro—NH$_2$[c] | 284 | MH$^+$ = 285 FAB | 10.5 8–40% B in 30 min. | 69% |
| (Gly—Nleu—Pro)$_9$—NH$_2$ | 2423 | MH$^+$ = 2422 FAB | 18.5 20–70% B in 30 min. | 4.3% |
| Ac—Gly—Nleu—Pro—NHCH$_3$[c] | 340 | MH$^+$ = 341 FAB | 12.2 7–70% B in 30 min. | 91% |
| Ac—(Gly—Nleu—Pro)$_3$—NH$_2$ | 860 | MH$^+$ = 861 FAB | 15.1 15–60% B in 30 min. | 8% |
| Ac—(Gly—Nleu—Pro)$_6$—NH$_2$ | 1663 | MH$^+$ = 1663 FAB | 17.3 15–80% B in 30 min. | 9% |
| Ac—(Gly—Nleu—Pro)$_{10}$—NH$_2$ | 2732 | MNa$^+$ = 2754 FAB | 14.8 30–90% B in 30 min. | 12% |

[a]Vydac C-18 column, 0.46 × 25 cm, flow rate: 1.0 ml/min.
[b]For those compounds prepared by solid phase methods, the yields were calculated based on the resin substitutions and the materials obtained from HPLC purification.
[c]Prepared by solution peptide synthesis methods.

An apparent advantage for the peptoid-containing collagen-like structures is that these analogs contain unnatural residues (peptoid residues) which enhance the biostability of these compounds. The peptide-peptoid collagen-like structures represent a new class of novel collagen-like biomaterials.

There will be various modifications, improvements, and applications of the disclosed invention that will be apparent to those skilled in the art, and the present application is intended to cover such embodiments. Although the present invention has been described in the context of certain preferred embodiments, it is intended that the full scope of the disclosure be measured only by reference to the following claims.

What is claimed is:

1. A heterotrimeric collagen-type polypeptide chain comprising at least one dipeptide-peptoid trimer and at least one tripeptide trimer wherein the dipeptide-peptoid trimer is independently selected from the group consisting of Gly-Xp-Pro and Gly-Pro-Xp wherein Xp and Yp are peptoid residues selected from N-substituted amino acids, provided that neither Xp or Yp is N-methylglycine; and wherein the tripeptide trimer is independently selected from the group consisting of Gly-Pro-Hyp and Gly-Pro-Pro; and wherein said heterotrimeric chain has a collagen-type helical configuration.

2. A heterotrimeric collagen-type polypeptide chain comprising a mixture of dipeptide-peptoid trimers, wherein each said trimer is independently selected from the group consisting of Gly-Xp-Pro and Gly-Pro-Yp wherein Xp and Yp are peptoid residues selected from the group consisting of N-substituted amino acids, provided that neither Xp or Yp is N-methylglycine, and wherein said heterotrimeric chain has a collagen-type helical configuration.

3. A synthetic collagen material having a collagen-like triple helical structure comprising at least one heterotrimeric collagen-type polypeptide chain according to claim 1.

4. A synthetic collagen material having a collagen-like triple helical structure comprising at least one heterotrimeric collagen-type polypeptide chain according to claim 2.

5. A synthetic heterotrimeric collagen-type polypeptide chain comprising a mixture of dipeptide-peptoid trimers, wherein each said trimer is independently selected from the group consisting of Gly-Xp-Pro and Gly-Pro-Yp; and wherein Xp and Yp are peptoid residues selected from the group consisting of N-substituted amino acids; provided that neither Xp nor Yp is N-methylglycine.

6. A synthetic heterotrimeric collagen-type polypeptide chain according to claim 5 further comprising at least one tripeptide trimer selected from the group consisting of Gly-Pro-Hyp and Gly-Pro-Pro.

7. A synthetic heterotrimeric collagen-type polypeptide chain according to claim 5 or 6 wherein Xp and Yp are independently selected from the group consisting of N-substituted peptoid isomers of valine, leucine, isoleucine, glutamine, lysine, phenylalanine and aspartic acid.

8. A synthetic heterotrimeric collagen-type polypeptide chain according to claim 7 wherein Xp is selected from the group consisting of N-butyl isoleucine leu), N-isopropyl glycine (Nval) and N-sec-butyl glycine (Nile) and Yp is selected from the group consisting of N-isopropyl glycine (Nval) and N-sec-butyl glycine.

9. A synthetic heterotrimeric collagen-type polypeptide chain according to any one of claims 1, 2, 3, 4, 5, or 6, said chain having an amino terminal end and a carboxy terminal end, wherein said amino terminal end is covalently attached to an acidic group X selected from the group consisting of linear, branched, saturated or unsaturated aliphatic acids, aromatic carboxylic acids and arailyl carboxylic acids, and wherein said carboxy terminal end is covalently attached to an amino group Y selected from the group consisting of ammonia, linear, branched, saturated or unsaturated aliphatic amines, aromatic amines and aralkyl amines.

10. A synthetic heterotrimeric collagen-type polypeptide chain according to claim 9 wherein X is an acetyl group and Y is selected from the group consisting of amide, bipyridine and maleimide.

* * * * *